(12) United States Patent
Fukuda

(10) Patent No.: US 11,648,156 B2
(45) Date of Patent: May 16, 2023

(54) URINE ABSORPTION PAD SYSTEM FOR MEN

(71) Applicant: IP GIKEN LLC, Nagoya (JP)

(72) Inventor: Yuichi Fukuda, Nagoya (JP)

(73) Assignee: IP GIKEN LLC, Nagoya (JP)

( * ) Notice: Subject to any disclaimer, the term of this patent is extended or adjusted under 35 U.S.C. 154(b) by 0 days.

(21) Appl. No.: 17/817,664

(22) Filed: Aug. 5, 2022

(65) Prior Publication Data

US 2022/0378629 A1 Dec. 1, 2022

Related U.S. Application Data

(63) Continuation of application No. PCT/JP2021/000597, filed on Jan. 11, 2021.

(30) Foreign Application Priority Data

Mar. 3, 2020 (JP) .................................. 2020-035526
Jul. 20, 2020 (JP) .................................. 2020-123461

(51) Int. Cl.
*A61F 13/475* (2006.01)
*A61F 13/513* (2006.01)
(Continued)

(52) U.S. Cl.
CPC ........ *A61F 13/4752* (2013.01); *A61F 13/513* (2013.01); *A61F 13/51456* (2013.01);
(Continued)

(58) Field of Classification Search
CPC .. A61F 13/471; A61F 13/475; A61F 13/4752; A61F 13/494; A61F 13/513;
(Continued)

(56) References Cited

U.S. PATENT DOCUMENTS 5,702,381 A * 12/1997 Cottenden ............. A61F 13/471
604/385.01
6,605,752 B2 * 8/2003 Magnusson ......... A61F 13/4756
604/385.01
(Continued)

FOREIGN PATENT DOCUMENTS

JP H02-096120 U 7/1990
JP H06-021626 A 3/1994
(Continued)

OTHER PUBLICATIONS

International Search Report and Written Opinion (Application No. PCT/JP2021/000597) dated Mar. 30, 2021 (with English translation).
(Continued)

*Primary Examiner* — Michele M Kidwell
(74) *Attorney, Agent, or Firm* — Burr Patent Law, PLLC

(57) ABSTRACT

A urine absorption pad for preventing leakage of urine is provided. A urine absorption pad includes: a front surface sheet (16) which has water permeability and contacts a skin; a back surface sheet (17) which has water impermeability and contacts underwear; an absorbent (18) which is sandwiched between the front surface sheet (16) and the back surface sheet (17) and absorbs urine having passed through the front surface sheet (16); and a guide A (11) and a guide B (12) which allow urine to permeate and are self-standing so as to rise to the front surface sheet (16) side with respect to the absorbent (18) to control flow of urine. The guide A (11) is arranged at an edge portion, and the guide B (12) is arranged so as to extend in a left-right direction.

2 Claims, 16 Drawing Sheets

(51) Int. Cl.
*A61F 13/537* (2006.01)
*A61F 13/15* (2006.01)
*A61F 13/514* (2006.01)
*A61F 13/53* (2006.01)

(52) U.S. Cl.
CPC .... *A61F 13/5376* (2013.01); *A61F 13/53717* (2013.01); *A61F 2013/15121* (2013.01); *A61F 2013/15463* (2013.01); *A61F 2013/530437* (2013.01)

(58) Field of Classification Search
CPC ............... A61F 13/51456; A61F 13/53; A61F 13/53717; A61F 13/5376; A61F 2013/15121; A61F 2013/15463; A61F 2013/530437; A61F 5/453; A61F 2013/15146; A61F 13/491; A61F 13/453
See application file for complete search history.

(56) References Cited

U.S. PATENT DOCUMENTS

| | | | | |
|---|---|---|---|---|
| 7,037,298 B2* | 5/2006 | Ohshima | ............ | A61F 13/4752 604/385.01 |
| 7,404,810 B2* | 7/2008 | Toro | ................. | A61F 13/4755 604/374 |
| 7,993,318 B2* | 8/2011 | Olsson | ............... | A61F 13/4915 604/385.19 |
| 8,889,946 B2* | 11/2014 | Hermansson | ....... | A61F 13/4752 604/374 |
| 8,926,578 B2* | 1/2015 | Drevik | ............... | A61F 13/5611 604/347 |
| 9,456,935 B2* | 10/2016 | Greening, II | ..... | A61F 13/49473 |
| 10,478,350 B2* | 11/2019 | Ruman | ................. | A61F 13/471 |
| 2003/0114805 A1* | 6/2003 | Rainville-Lonn | ........................... | A61F 13/5605 604/358 |
| 2004/0097893 A1* | 5/2004 | Elfstrom | ................. | A61F 5/453 604/349 |
| 2005/0137552 A1* | 6/2005 | Hansson | ............... | A61F 13/493 604/385.01 |
| 2005/0267426 A1* | 12/2005 | Shedrick | ............... | A61F 13/471 604/347 |
| 2006/0287635 A1* | 12/2006 | Angel, Jr. | ............. | A61F 13/532 604/385.01 |
| 2007/0043330 A1 | 2/2007 | Lankhof et al. | | |
| 2008/0195071 A1* | 8/2008 | Ponomarenko | ... | A61F 13/51113 604/385.24 |
| 2013/0096525 A1* | 4/2013 | Hermansson | ....... | A61F 13/4752 604/374 |
| 2015/0282998 A1* | 10/2015 | Arizti | ................ | A61F 13/51104 604/385.19 |
| 2022/0273502 A1* | 9/2022 | Takahira | ............. | A61F 13/4704 |

FOREIGN PATENT DOCUMENTS

| | | |
|---|---|---|
| JP | 3078455 U | 7/2001 |
| JP | 2011-067407 A | 4/2011 |
| JP | 3171928 U | 11/2011 |
| JP | 2012-095790 A | 5/2012 |
| JP | 5433815 B1 | 3/2014 |
| JP | 2014-140613 A | 8/2014 |
| JP | 2016-042946 A | 4/2016 |
| JP | 2019-146657 A | 9/2019 |
| JP | 2019-162300 A | 9/2019 |

OTHER PUBLICATIONS

International Preliminary Report on Patentability (Chapter II) (Application No. PCT/JP2021/000597) dated Nov. 22, 2021 (with English translation).

\* cited by examiner

URINE ABSORPTION PAD SYSTEM FOR MEN

TECHNICAL FIELD

The present invention relates to a urine absorption pad that is worn in front of the genitalia and absorbs urine to be discharged.

BACKGROUND ART

Urine absorption pads (hereinafter, also simply referred to as pads) are known from a number of commercial products. For urine absorption, in addition to the pad, there is also pants type. Regarding the pants type, there is a low possibility that discharged urine leaks to the outside of the pants and there is no concern that clothes are stained, but wearing and replacement thereof are exactly the same as in pants and troublesome, which makes is difficult to use the pants type when going out. In addition, as compared to the pad, the pants type includes many parts other than the part directly contributing to urine absorption, has a large weight and shape, is inconvenient for carrying, and has an excessive environmental load at the time of disposal.

On the other hand, an existing pad type is compact with a substantially entire part directly contributing to urine absorption, and wearing and replacement thereof are easy. However, the method of absorbing urine, especially in the pad for men, is incomplete. Therefore, the existing pad type cannot absorb the entire amount of 150 cc to 200 cc of one voided volume of an adult male, so the reliability is low, and as a result, it is used at most for absorbing residual urine after urination.

It is considered that the incompleteness of the pad for men is caused by a design concept that is not much different from that for women although it is for men. There are the following two points to be noted that the pad for men is largely different in the design from the pad for women. First, the urine release direction is perpendicular to the pad plane in the case of the pad for women, whereas the urine release direction is parallel to the pad plane and the direction is not fixed in the case of the pad for men. Second, the scrotum (hereinafter, "balls") is present immediately below where urine is released. The positional relationship is: urethral opening→balls→absorbent in the rear side of the pad. For this reason, the balls become an obstacle, and the released urine does not reach the absorbent in the rear side of the pad but stagnates on the upper surface of the front side of the pad, and when the released urine exceeds the urine absorption capacity of the absorbent in this portion, the urine overflows to the outside of the pad system. In addition, the balls press the pad surface to hinder the flow of urine in the pad, which causes unabsorbed urine to overflow from the front or lateral side of the pad although sufficient urine absorption capacity remains in the rear side of the pad. The pad for men should be designed with in mind that the gap between the pad wearer and the pad is very narrow when the pad is worn. Here, the front side of the pad is a side close to the wearer's head in the direction of the wearer's height in the pad worn by the wearer, and the rear side is a side close to the wearer's foot in the direction of the wearer's height.

For treatment of frequent urination, it is recommended to endure urination as much as possible rather than using drugs. However, in many cases, he endures urination until the last minute before leaking, and when he enters the toilet, urination immediately starts before he lowers his/her pants. This urination cannot be stopped until the urine has run out (hereinafter, also referred to as "irresistible leakage"). For this reason, the recommended treatment method of "enduring as much as possible" cannot be implemented unless there is a guarantee that the pad reliably captures the entire amount of urine. The existing pat, while having a sufficient absorbent, fails to capture one voided volume of 150 cc to 200 cc of an adult male due to a lack of the design concept mentioned above, and is useless for this treatment.

CITATIONS LIST

Patent Literature

Patent Literature 1: Japanese Utility Model Registration No. 3171928
Patent Literature 2: JP 5433815 B2
Patent Literature 3: JP 2019-146657 A
Patent Literature 4: JP 2016-42946 A

SUMMARY OF INVENTION

Technical Problems

Patent Literature 1 relates to a disposable absorbent article such as an adult incontinence pad, but does not consider the above-described two points to be noted of the pad for men. In FIGS. 5A and 5B, part numbers 83 and 85 are shown as tentative shielding walls, but these are sheet-like ones called "leg cuff sheets", and it is assumed that a woven fabric material, a nonwoven fabric material, or the like is suitably used (see paragraph [0054]). They are insufficient for blocking urine released from a direction parallel to a pad plane from going outside the system, cannot store urine even temporarily, and allow urine to overflow.

Patent Literature 2 relates to a urine absorption pad for men. When the pad is worn, the penis is inserted into the first space portion 72 provided in the lower side of the pad, so that the excreted urine is prevented from leaking to the outside of the system (see paragraph [0029]). In addition, when the penis is directed upward, the second space portion 73 provided in the upper side of the pad receives the excreted urine and prevents leakage of the urine to the outside of the system (see paragraph [0033]). Furthermore, for side leakage, the barrier cuff sheet 50 is erected to form a three-dimensional cuff, thereby effectively preventing leakage of urine (see paragraph [0033]).

The above-described pad can be expected to have a certain level of effect when the wearer does not move, such as when the wearer is in a bedridden state. However, when the wearer performs daily activities, a problem occurs and it becomes uncertain to prevent leakage of urine to the outside of the system. That is, when the wearer performs daily activities, although close contact between the pad and the wearer is maintained with high sureness, sliding in the longitudinal direction of the body inevitably occurs. When walking or particularly when standing up or sitting down, there is a risk that the penis may come out of the first space portion 72 due to sliding in the longitudinal direction between the body and the pad. Here, the longitudinal direction is a direction of the wearer's height in a state where the wearer wears the urine absorption pad.

Through experiment of the above matter, Patent Literature 2 assumes the situation that the penis is directed upward (the penis comes out of the first space portion 72). However, it is sufficiently assumed that the penis comes out of the first space portion 72, but the penis is not directed upward and does not return to the first space portion 72, and the penis is positioned outside the cover sheet 61. Since the cover sheet 61 is formed of liquid hardly-permeable or liquid non-permeable fiber nonwoven fabric or the like (see paragraph [0028]), urine is not absorbed when the penis is positioned outside the cover sheet 61, leading to leakage of all urine.

Even in the case where the penis is directed upward as assumed in Patent Literature 2, it is uncertain whether the penis reliably enters the second space portion 73 provided in the upper part of the pad, which also leads to leakage of urine, so that the reliability is low. Furthermore, the barrier cuff sheet 50, which claims to prevent side leakage, is highest at the central portion of the pad, but has a low height at the upper portion and the lower portion of the pad where the probability of side leakage is high (see FIG. 6), which also reduces the reliability. This is because it seems that there is a considerably low chance of releasing urine while the penis is directed to the side.

Although the position of the balls is shown in FIG. 8 of Patent Literature 2, the pressing of the balls against the pad main body is not considered. That is, Patent Literature 2 does not recognize the problem peculiar to the existing pad for men that the balls hinder uniform absorption of urine into the entire pad and the capacity of the prepared absorbent cannot be exhibited by 100%, which leads to leakage of urine to the outside of the system.

As in Patent Literature 2, there are other prior Patent Literatures in which a penis is housed in a pocket shape (for example, Japanese Utility Model Registration No. 3078455), but leakage of urine cannot be prevented for the same reason as in Patent Literature 2.

Patent Literature 3 also discloses a urine absorption pad for men. A "three-dimensional gather" is used to prevent the side leakage, and the three-dimensional gather includes a three-dimensional gather sheet and a stretchable elastic member (see paragraph [0048]), and is not different from Patent Literature 2 in this respect. As described in the latter part of paragraph [0011] of the present specification, the pad is highest at the central portion of the pad, but has a low height at the upper portion and the lower portion of the pad where the probability of side leakage is high, which reduces the reliability. This is because, as described above, it seems that there is a considerably low chance of releasing urine while the penis is directed to the side.

Patent Literature 3 discloses a body fluid leakage test (see paragraph [0061]). The literatures listed in the present application other than Patent Literature 3 do not disclose a result of a leakage test, and therefore, apprehension cannot be eliminated that they may have been filed and published without being aware of the above-described two points that are important in designing a pad for men cannot be dispelled. This is because the real effect has to be questioned. On the other hand, although the body fluid leakage test is disclosed in Patent Literature 3, it is a test in which the pad is fixed on an inclined plate and saline is allowed to flow down thereon (see paragraph [0061]), which is not an actual wearing experiment. Thus, the real effect is unknown.

In Patent Literature 4, an upper absorber 25U is provided as a guide. This is "made of fluff pulp and super absorbent polymer (SAP)" (paragraph [0024]).

The upper absorber 25U is provided to "be formed into a substantially V shape to be adaptable to a urination position of men which is unstable in the underwear P." (paragraph [0033]), and is not a guide for controlling the flow of released urine.

Furthermore, since the upper absorber 25U formed into a substantially V shape is made of fluff pulp and SAP, which is a "super absorbent resin" (paragraph [0024]), the upper absorber 25U quickly absorbs the flowing urine and increases in volume. For this reason, as described above, although, when the pat is worn, the gap between the pad wearer and the pad is already very narrow and urine flow in the pad is poor, a large obstacle is generated. As a result, in a case where there is a large amount of urine, the urine does not flow rearward but stagnates in front and overflows while the rear absorbent remains. In Patent Literature 4, this phenomenon is regarded as being no problem in the case of mild urine leakage, and it is described that "leakage along the rear side can be prevented" (paragraph [0033]). That is, the rear absorbent is not used to absorb the entire amount of urine. This is because Patent Literature 4 is directed to "mild urine leakage" (paragraph [0002]).

In addition, Patent Literature 4, although it is also a specification of a chemical field in which an effect is produced by a chemical change caused by a chemical reaction, does not disclose an actual pad wearing experiment as an example. Thus, the real effect is unknown.

Solutions to Problems

A urine absorption pad according to the present invention includes: a front surface sheet that has water permeability and contacts a skin; a back surface sheet that has water impermeability and contacts underwear; an absorbent that is sandwiched between the front surface sheet and the back surface sheet and absorbs urine having passed through the front surface sheet; and two types of guides, a guide A and a guide B, that are self-standing so as to rise to the front surface sheet side with respect to the absorbent, and allow urine to permeate to control flow of urine. The guide A and the guide B are separate bodies, are porous bodies that are continuous voids and have water permeability, and do not contain a superabsorbent polymer. The guide A has higher water retainability than the guide B, has water impermeability at an outermost surface facing an outside of a system, and prevents overflow of urine to the outside of the system. The guide B has a U shape and is arranged so as to extend in a left-right direction, and the guide A is arranged at an edge portion and extends below the guide B.

The term "self-standing" as used herein refers to holding a state of being self-standing so as to rise by itself rather than in a film form. The guide in the present invention has a predetermined number (about several millimeters) of cross-sectional thickness in a standing direction, and not only has a function as an obstacle but also can contain voids that allow urine to permeate and can retain water, and has a function of controlling flow of urine by temporarily storing urine in the guide, forming a flow path in the guide, or the like. The term "temporarily" as used herein means a predetermined time. A general pad has a structure in which an absorbent fixes moisture of several tens to a hundred of times the volume of the absorbent by a chemical change, but this fixing greatly changes the volume of the absorbent at the absorbing portion. Therefore, when the guide contains even a small amount of this substance that chemically fixes the moisture, the guide expands and changes its appearance, not only becomes a so-called obstacle and loses the function of controlling the flow of urine, but also hinders diffusion of urine in the pad, easily leading to urine leakage with a small amount of urine. In contrast, the guide in the present invention does not contain a superabsorbent polymer component that fixes urine by a chemical change.

In addition, in many Patent Literatures, a guide for preventing side leakage of urine is a sheet or a film-like guide, which is flat before the pad is worn, and is suspended by an elastic body such as rubber, and bent after the pad is worn and becomes an upright state for the first time, thereby aiming to function as an obstacle for preventing overflow of urine. Such a guide is not perfect since urine may leak as described in paragraph [0011] of the present specification.

In order to prevent overflow of urine to the outside of the system, preferably, the guide is self-standing, is a porous body which is continuous voids and has water permeability, and has flexibility because it may directly touch the skin, and specifically is a spongy synthetic resin that can retain water. The guide temporarily absorbs and stores urine to prevent overflow of the urine to the outside of the system (hereinafter, also referred to as a "guide A"). Here, the term "outside of the system" refers to a space outside the urine absorption pad in a direction along the attachment surface of the guide.

In order to confirm the water retainability of the guide A, an immersion test was performed. The results of the immersion experiment are shown below. As the guide A, "GEKI-OCHI (registered trademark) PAPA" S-693 manufactured by LEC, INC. was selected.

TABLE 1

|  | Dry State | Water-retained State | Water Retention Ratio |
| --- | --- | --- | --- |
| Guide A: Spongy | 13 g | 499 g | 38.4 |

The outer shape of the guide A was 15 mm square×125 mm. The length of 125 mm was set to be the same as the length of the guide B described later. 20 pieces of the guide A having an outer shape of this dimension were prepared, and the weight thereof was measured and found to be 13 g. After the guides A were arranged so as not to overlap in a kitchen tray, shower water was discharged thereto from about 30 cm above the kitchen tray. Since the guides A had high water absorbency, the entire guides A absorbed water and retained water without difficulty. Thereafter, the guides A retaining water were taken out from the kitchen tray, and left for 1 minute with the long-side direction being the vertical direction. There was almost no water dripping from the guides A while being left, and after 1 minute since the guides A were left, a water-retained state was maintained without dripping. Thereafter, the weight of the 20 pieces of the guide A in the water-retained state was measured and found to be 499 g. The value obtained by dividing the weight in the water-retained state after immersion by the weight in the dry state (water-unretained state) was 38.4. This value is defined as a water retention ratio, which is a numerical value indicating a level of water retainability. The guides A had a water retention ratio of 38.4. In addition, since the guide A does not contain a component that fixes moisture by a chemical change, no shape change (swelling or the like) was visually observed between the dry state and the water-retained state after immersion. Since the guide A is spongy, that is, in a state in which the continuous voids in the main body of the guide A are formed in such a manner that a plurality of bubbles are connected, the above effect is exhibited.

When the urine absorption pad is vertically long, it is desirable that the guides A is arranged at both left and right edge portions which are edge portions of the pad. Furthermore, it is desirable that the outermost surfaces which are the outer surfaces of the left and right guides A and the surfaces facing the outside of the system have water impermeability. Since the guide A is self-standing so as to rise, the guide A has a certain height even on the upper side or the lower side of the pad, and can prevent overflow of urine.

Further, when the urine absorption pad is horizontally long, it is desirable that the guide A is arranged at an uppermost edge portion in the longitudinal direction which is an edge portion of the pad. Furthermore, it is desirable that the outermost surface which is the outer surface of the guide A and the surface facing the outside of the system has water impermeability. Since the guide A is self-standing so as to rise, the guide A has a certain height even after the pad is worn, and can prevent overflow of urine even when urine is released upward.

Since the guide A is a porous body which is continuous voids and has water permeability, the guide A can also retain and store a certain amount of urine released toward the guide A, and further contributes to prevention of overflow of urine. In addition, the guide A is sponge-like. Therefore, when the pad is vacuum-packaged, the volume is reduced and the pad becomes compact, and when taken out from the packaging, the guide A rises up under the external pressure and exerts the original function as a shielding wall.

The other of the two types of guides is a guide which has a predetermined width, and is self-standing so as to rise to the front surface sheet side with respect to the absorbent to control flow of urine, and in order to be able to guide surging urine to other portions in the pad, it is desirable that the guide has water permeability, hardly allow urine to stagnate therein, has low flow path resistance with respect to the flow of urine, allows urine to flow inside, and guides urine to other regions. Specifically, a material in a state where a polymer material such as a synthetic resin is formed into a fibrous form and the fibers are intertwined and integrated in a three-dimensional shape so that the fibers are entangled (specifically, it is a loofah sponge shape made from a loofah plant) is preferable (hereinafter, also referred to as a "guide B"). In the guide B, the size of the continuous voids formed therein is larger than that of the guide A so that urine is less likely to stagnate therein and the flow path resistance is low with respect to the flow of urine.

In order to confirm the water retainability of the guide B, an immersion test was performed. The results of the immersion experiment are shown below. As the guide B, "GEKI-OCHI-KUN" (registered trademark) K00213 manufactured by LEC, INC. was selected.

TABLE 2

|  | Dry State | Water-retained State | Water Retention Ratio |
| --- | --- | --- | --- |
| Guide B: Loofah Spongy | 19 g | 36 g | 1.9 |

The shape of the guide B was φ 18 mm×125 mm. 20 pieces of the guide B having this shape were prepared, and the weight thereof was measured and found to be 19 g. After the guides B were arranged so as not to overlap in a kitchen tray, shower water was discharged thereto from about 30 cm above the kitchen tray, the guides B were pressed by hand into the kitchen tray in which water was sufficiently stored, so that water was made to sufficiently permeate the guides B. Thereafter, the guides B containing sufficient water were taken out from the kitchen tray, and left for 1 minute with the long-side direction being the vertical direction. While the guides B were left, a large amount of water dripped from the guides B, but the dripping stopped in about 1 minute and an equilibrium state was obtained, so that the left time was set to 1 minute. Thereafter, the weight of the 20 guides B was measured and found to be 36 g. The water retention ratio of the guide B was 1.9. In addition, since the guide B does not contain a component that fixes moisture by a chemical change, no shape change (swelling or the like) was visually observed between the dry state and the water-retained state after immersion.

In order to compare the degree of water retainability with the guide A, when the water retention ratios indicating the respective water retainability are viewed, the guide A is considerably higher than the guide B. With high water retainability, the guide A absorbs surging urine, and changes the flow direction while reducing the flow strength, thereby preventing overflow of urine from the guide A to the outside of the system. By arranging the guide B such that the long-side direction of the guide B is set in a lateral direction, that is, so as to extend in the left-right direction of the pad, the guide B exerts a function not only to make urine that has permeated any portion of the guide B immediately pass through the guide B in the short-side direction of the guide B, but also to make a part of the urine that has permeated remain in the guide B and flow in the lateral direction (long-side direction). Since the guide B has lower water retainability (water retention ratio) of urine than that of the guide A, the inside of the guide B serves as a urine flow path. Urine can be guided to a desired position in the pad by appropriately adjusting the arrangement position of the guide B in the pad.

It is preferable that the guide B is arranged at an arbitrary position on the urine absorbent other than the edge portion of the pad. When the guide B is arranged along the inside of the guide A, it is possible to reliably guide urine blocked by the guide A to the lower side of the pad.

In addition, by arranging the guide B at the central portion of the pad so as to extend nearly horizontally in a lateral direction, that is, in the left-right direction of the pad, in a U shape, even when urine is released to, for example, one side in the lateral direction in the pad, the urine can be dispersed to the other side in the lateral direction in the pad by the guide B. In order to make the guide B exert a function as the urine flow path, arrangement in both the longitudinal direction and the lateral direction is also preferable as described above. Here, the lateral direction is a direction orthogonal to the height of the wearer and a direction along a surface on which the pad spreads in a state where the wearer wears the urine absorption pad. Therefore, a U shape or an H shape is suitably used as the shape for arranging the guide B.

Advantageous Effects of Invention

According to the embodiment of the urine absorption pad for men according to the present invention, the guide A which is self-standing so as to rise and has a certain height is provided at the outermost edge portion which is the edge portion of the pad. Therefore, even if urine is released in any direction of the penis in daily operations after wearing the pad, the guide A receives urine while absorbing the urine since the guide A is a porous body which is continuous voids and has water permeability.

Since the outermost surface of the water-permeable guide A which is the outer surface facing the outside of the system, has water impermeability, the urine that has flowed in can be blocked and changed in direction, so that the guide A can serve as a guide for preventing leakage and overflow of urine.

When the urine absorption pad has a vertically long shape, the guides A are arranged in the longitudinal direction of the left and right of the pad, and thus, urine blocked by the water-impermeable surface mostly flows downward along the guides A and is absorbed and fixed by the absorbent present therein. It is further preferable that the guide B is provided inside along the guide A. Since the guide B is formed in such a state that fibrous polymer material is entangled and intertwined into a three-dimensional shape and a large number of continuous voids are formed therein, the guide B serves as a transport pipe, resists pressing of the balls that hinders flow of urine in the pad, and transports urine to the absorbent present behind the balls, so that the absorbent present there fixes urine and prevents leakage of urine.

Even when the penis is deflected to the right or left, urine is distributed in both the right and left directions (that is, in the lateral direction) in the pad by the guide B extending in the left-right direction of the pad at the central portion of the pad and arranged in a substantially horizontal lateral direction or in a U shape. Thus, since urine is distributed over the entire pad by the presence of the guides, and urine is fixed by using the capacity of all the absorbents, the pad, while being compact, can absorb 150 cc to 200 cc of one voided volume of an adult male with a margin.

In addition, when the urine absorption pad has a horizontally long shape, the guide A is arranged at the uppermost edge portion in the longitudinal direction which is the edge portion of the urine absorption pad, and the guide A is self-standing so as to rise. Therefore, even after the pad is worn, the guide A has a certain height, and can prevent overflow of urine even when urine is released upward since the outermost surface which is the surface facing the outside of the system has water impermeability.

When the urine absorption pad has a horizontally long shape, urine is distributed in both the right and left directions (that is, in the lateral direction) in the pad by the guide B extending in the left-right direction of the pad at the central portion of the pad and arranged nearly horizontally in a lateral direction or in a U shape. Thus, since urine is distributed over the entire pad by the presence of the guides, and urine is fixed by using the capacity of all the absorbents, the pad, while being compact, can absorb 150 cc to 200 cc of one voided volume of an adult male with a margin.

As a result, the pad can cope with so-called "irresistible leakage", which makes it possible to practice "enduring as much as possible" anywhere which is recommended for frequent urination treatment, and in particular, enables middle-aged men to re-enter the society without using drugs. In addition, with the convenience of being easily detachable, highly reliable, and capable of urinating urine anywhere, the pad can be expected to be effective not only for treatment and care purposes but also for improving the quality of life serving as a simple detachable toilet for leisure such as hiking and mountain climbing where it is difficult to find a toilet, for a long-distance drive, and for a long-time theater, etc. That is, it is possible to provide a new lifestyle in which a toilet is carried and used as a "pad toilet" regardless of the surrounding environment for urination.

DESCRIPTION OF EMBODIMENTS

First Embodiment

Figure 1:
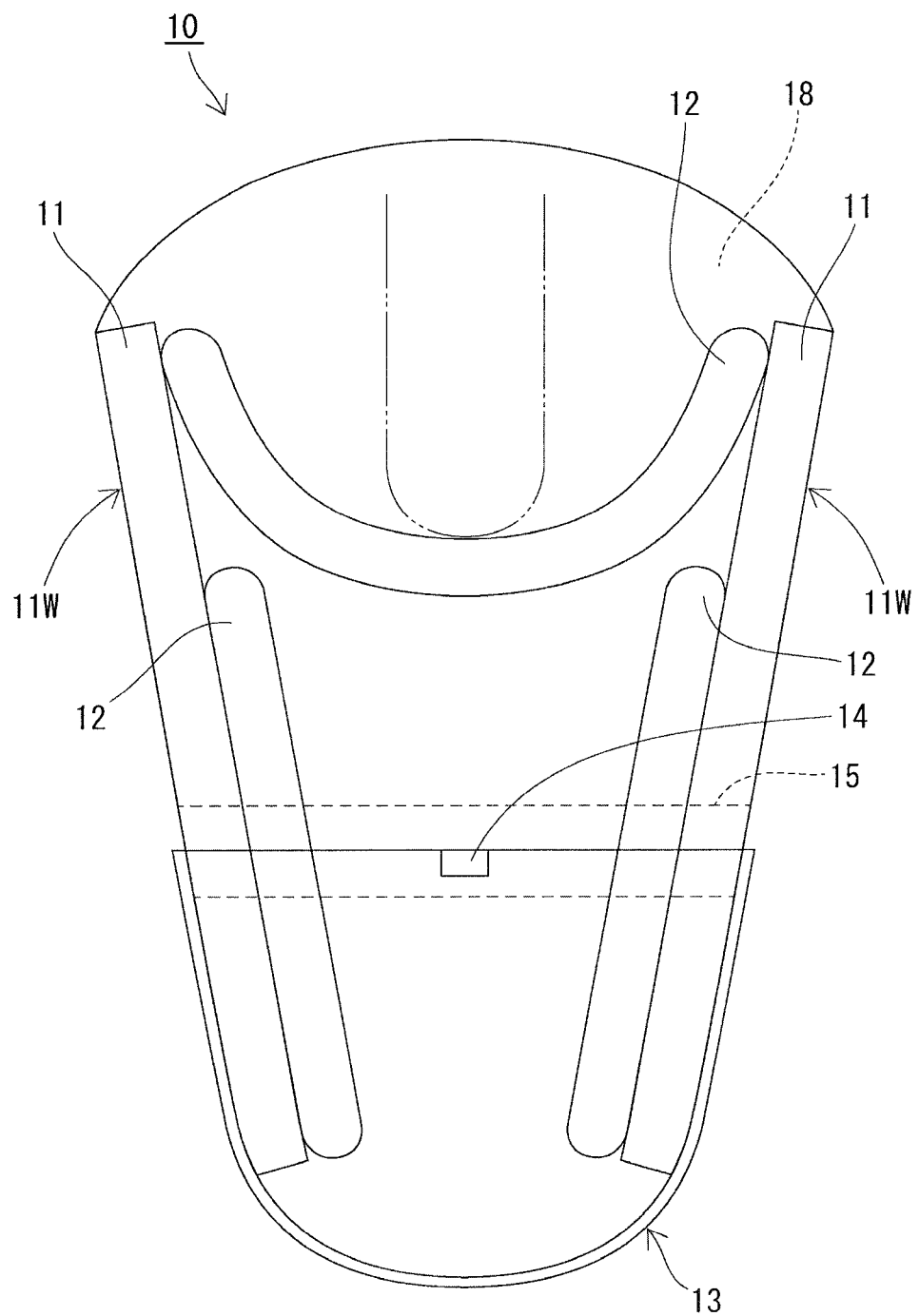
FIG. 1 is a plan view of a urine absorption pad according to a first embodiment of the present invention.
Figure 2:
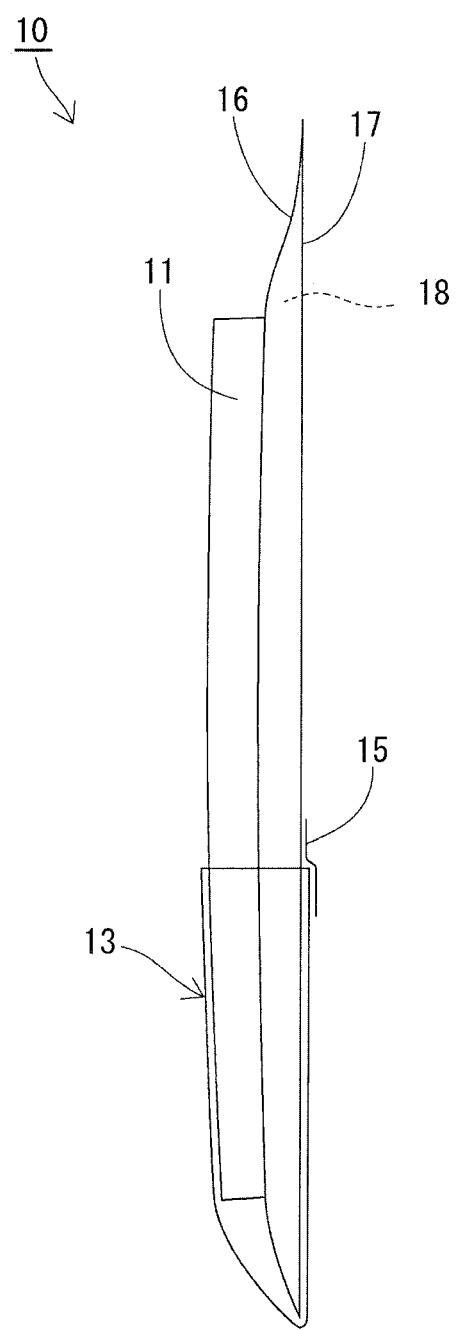
FIG. 2 is a side view of the urine absorption pad according to the first embodiment of the present invention.
Figure 3:
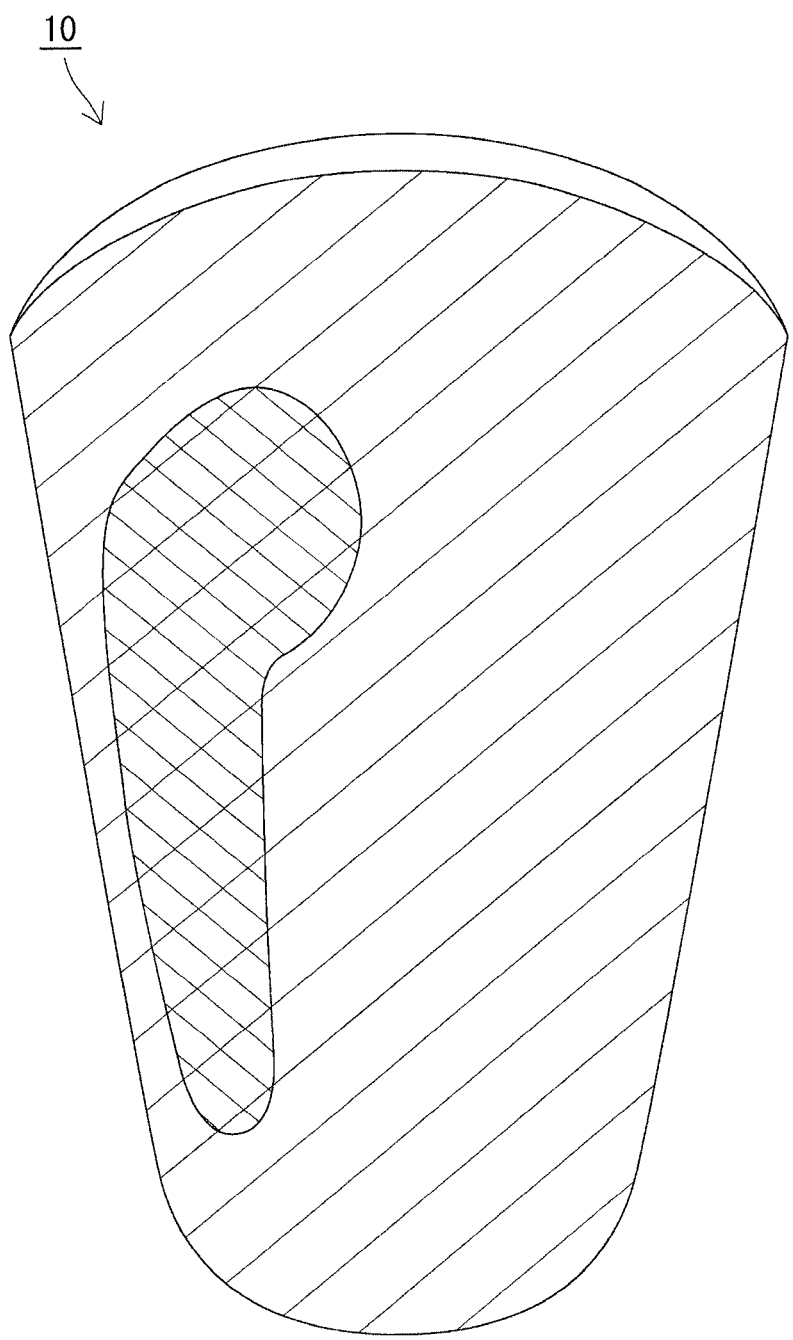
FIG. 3 is a schematic view of a urine absorption status in the first embodiment of the present invention.

FIGS. 1 to 3 show an example of a urine absorption pad according to the present invention. FIG. 1 is a plan view of the pad according to the present invention, FIG. 2 is a side view thereof, and FIG. 3 is an overview of a reaction status of an absorbent 18 with a front surface sheet removed after a use experiment of the pad.

Reference numeral 10 in FIG. 1 denotes a urine absorption pad for men for realizing the present invention, and "Poise (registered trademark) Men's Pad" Thin and Wide 300 cc manufactured by NIPPON PAPER CRECIA Co., LTD. is used as a base material thereof. A portion corresponding to a barrier cuff sheet (Reference numeral 50 of Patent Literature 2) is removed before various guides and the like were attached. This is because the portion has water impermeability and may hinder urine absorption.

Reference numeral 11 denotes a guide A, and a cellophane tape is stuck to the outer surface which is the surface facing the outside of the system to make the surface have water impermeability. Reference numeral 11W represents the outer surface having water impermeability. As a result, the guides A 11 stuck to a front surface sheet 16 can prevent overflow of urine to the outside of the system (that is, the outside of the urine absorption pad) beyond the outer surfaces 11W. As the guide A, "GEKIOCHI (registered trademark) PAPA" S-693 manufactured by LEC, INC. is appropriately cut and formed into a 15 mm square to be used. This is spongy and can be easily impregnated with water. Reference numeral 12 denotes a guide B, and in the first embodiment, three guides B are arranged. As the guide B, a cylindrical portion having a diameter of about 18 mm of "GEKIOCHI-KUN" (registered trademark) K00213 manufactured by LEC, INC. is appropriately divided and cut to be used. This is a so-called loofah sponge shape in which synthetic resin fibers are intertwined and integrated. The guide A 11 (i.e., guide A of reference No. 11) and the guide B 12 (i.e., guide B of reference No. 12) can control the flow of urine in the urine absorption pad 10. The guide A 11 and the guide B 12 are both porous bodies which are continuous voids and have water permeability. The size of one void in the continuous voids of the guide A 11 is smaller than that of one void in the continuous voids of the guide B 12. Therefore, as compared with the guide B 12, the guide A 11 is more likely to temporarily store the urine that has permeated and has been absorbed therein. On the other hand, as compared with the guide A 11, the guide B 12 has lower performance of temporarily storing the urine that has permeated, so that the urine easily flows therein. Thus, the guide B 12 stuck to the front surface sheet 16 can guide urine to other regions in the urine absorption pad 10.

The guides A 11 and the guides B 12 are stuck to the surface of the urine absorption pad for men 10 using a double-sided tape. As the double-sided tape, "Scotch (registered trademark) strong double-sided tape" KB-10 manufactured by 3M Japan Limited is used. Therefore, the surfaces of the guides A and B in contact with the pad have water impermeability. The guides A 11 and the guides B 12 are stuck to the wearer's skin side of the front surface sheet 16 so as to be self-standing and so as to rise to the front surface sheet 16 side with respect to a back surface sheet 17. The guide A 11 and the guide B 12 are formed in a band shape. The guide A 11 and the guide B 12 each have a predetermined width in the short-side direction that is orthogonal to the long-side direction of the band shape and along the surface where the front surface sheet 16 spreads.

Reference numeral 13 denotes a kitchen plastic bag. This is for guiding urine to prevent urine leakage from the lower end of the pad of the present invention when urine reaches the lower end in a liquid state before being absorbed by an adsorbent. Reference numeral 14 is a double-sided tape, and is used for sticking the opening of the plastic bag 13 to the front surface of the pad 10, since urine may leak from the opening portion of the plastic bag 13 if the opening portion is in a free state. The total weight of the pad of the present invention complete with these pieces of equipment is 32 grams.

A two-dot chain line in FIG. 1 is a penis placement position when wearing the pad according to the present invention. FIG. 2 is a side view of the pad of the present invention. Reference numeral 16 denotes a front surface sheet of the pad of the present invention, which is mainly a sheet having water permeability. The front surface sheet 16 contacts the skin of the wearer. Reference numeral 17 is the back surface sheet of the pad of the present invention, which has water impermeability. The back surface sheet 17 contacts underwear worn by the wearer. Between 16 and 17, the absorbent 18 for absorbing urine having passed through the front surface sheet 16 is contained. That is, the absorbent 18 is sandwiched between the front surface sheet 16 and the back surface sheet 17. It can be seen that the guide A 11 already has a certain height even in the vicinity of the upper end of the pad of the present invention. Reference numeral 15 denotes a cellophane tape, which closes the opening portion of the plastic bag 13 on the back surface side of the pad over the entire surface. The broken line 15 in FIG. 1 is the cellophane tape.

In the use experiment, the pad according to the present invention was attached to tight-fitting pants, and after about two and a half hours, a urine discharge experiment was performed in an upright posture with both legs opened to a substantially shoulder width. In this urine discharge experiment, no leakage of urine to the outside of the system was observed. The weight of the pad of the present invention after this experiment was 243 grams. Since the initial weight after sticking all of the various guides and the like was 32 g, the difference 211 g is the weight of urine, and assuming that the urine specific gravity is 1, 211 cc could be absorbed and captured without leaking to the outside of the system.

FIG. 3 is an overview of the reaction status of the absorbent 18 with the front surface sheet 16 removed after the experiment. The single hatched portion is a yellowed portion. A white unreacted portion slightly remains at the upper end of the pad, but substantially the entire surface of the pad is reacted. The double hatched portion is a portion that has been more deeply yellowed than the single hatched portion. As viewed from these, there is a possibility of further absorption of urine.

Slight water droplets were found in the plastic bag 13 after the use experiment. It can be seen that the released urine permeates the guides A 11 and the guides B 12 flows smoothly over the pad by the guides A 11 and the guides B 12, and is mostly captured by the absorbent 18 in the process, and a part thereof may directly reach the lower end of the pad. Therefore, the plastic bag 13 is considered to be a necessary guide element for preventing urine leakage, but it is not necessarily the plastic bag 13. At least, the plastic bag 13 is not necessary on the back surface sheet 17 side. In this experiment, the plastic bag 13 is used because of ease of processing, but in practice, it only needs to be present on the front surface sheet 16 side. Furthermore, instead of a bag shape, a water-impermeable guide film that covers a part of the guides A 11, the guides B 12, and the front surface sheet 16 may be used.

The results of repeated wearing tests using the same form as that of the first embodiment are shown in Table 3.

TABLE 3

| Experiment Number | Pad Weight (g) | | Urine Absorption Capturing Amount (cc) | Presence or Absence of Leakage to Outside of System | Sense of Use |
| --- | --- | --- | --- | --- | --- |
| | Before Wearing | After Urine Discharge Test | | | |
| Example 1 | 32 | 243 | 211 | Absent | Favorable |
| Example 2 | 32 | 239 | 207 | Absent | Favorable |
| Example 3 | 32 | 273 | 241 | Absent | Favorable |

In all cases, there was no leakage of urine to the outside of the system. The sense of use referred to herein is the sense of use after the wearing test, and in the first embodiment, there was a sense of wetness in the lower part of the penis and a part of the balls in contact with the penis after discharge of urine. However, there was no particular problem in the sense of use.

According to the first embodiment configured as described above, the following effects can be obtained.

The urine absorption pad 10 includes the front surface sheet 16 which has water permeability and contacts the skin, the back surface sheet 17 which has water impermeability and contacts underwear, the absorbent 18 which is sandwiched between the front surface sheet 16 and the back surface sheet 17 and absorbs urine having passed through the front surface sheet 16, and the guides A 11 and the guides B 12 which allow urine to permeate and are self-standing so as to rise to the front surface sheet 16 side with respect to the back surface sheet 17 to control the flow of urine. With this configuration, urine is guided to a wide range in the urine absorption pad 10 by the guides A 11 (having relatively high water retainability) and the guides B 12 (having relatively low water retainability) having different water retainability, so that the urine absorption capacity of the urine absorption pad 10 can be fully utilized.

The guide A 11 is a porous body which is continuous voids and has water permeability, temporarily absorbs and stores urine, and prevents overflow of urine to the outside of the system. With this configuration, it is also possible to store a certain amount of urine released toward the guides A 11, so that overflow of urine can be prevented. In addition, since the guide A 11 is a porous body (that is, sponge-like) which is continuous voids. Therefore, when the pad is vacuum-packaged, the volume is reduced and the pad becomes compact, not bulky.

The guide A 11 is spongy and has water permeability and retainability. With this configuration, since the continuous voids are formed such that air bubbles are continuous, urine can be efficiently stored. In addition, since the guide A 11 does not contain a chemical absorbent such as a superabsorbent polymer, the volume does not increase even when urine is stored, so that the guide A 11 does not become an obstacle to flowing urine and continues to function literally as a guide.

Since the guide B 12 also does not contain a chemical absorbent such as a superabsorbent polymer, urine flows inside the guide B 12 and is guided to other regions. With this configuration, the guide B 12 facilitates flow of urine inside, so that urine can be guided to a desired region in the pad. In addition, by arranging the guide B 12 along the guide A 11, urine whose overflow has been blocked by the guide A 11 can flow through the inside of the guide B 12. Thus, it is possible to efficiently absorb urine using the entire wide region of the pad while making urine flow well in the pad.

The guide B 12 has a loofah sponge shape in which synthetic fibers are intertwined and integrated, and does not contain a chemical absorbent. With this configuration, since the continuous voids are larger and the water retainability is lower than those of the guide A 11, the urine more easily flows inside the guide B 12.

Second Embodiment

Figure 4:
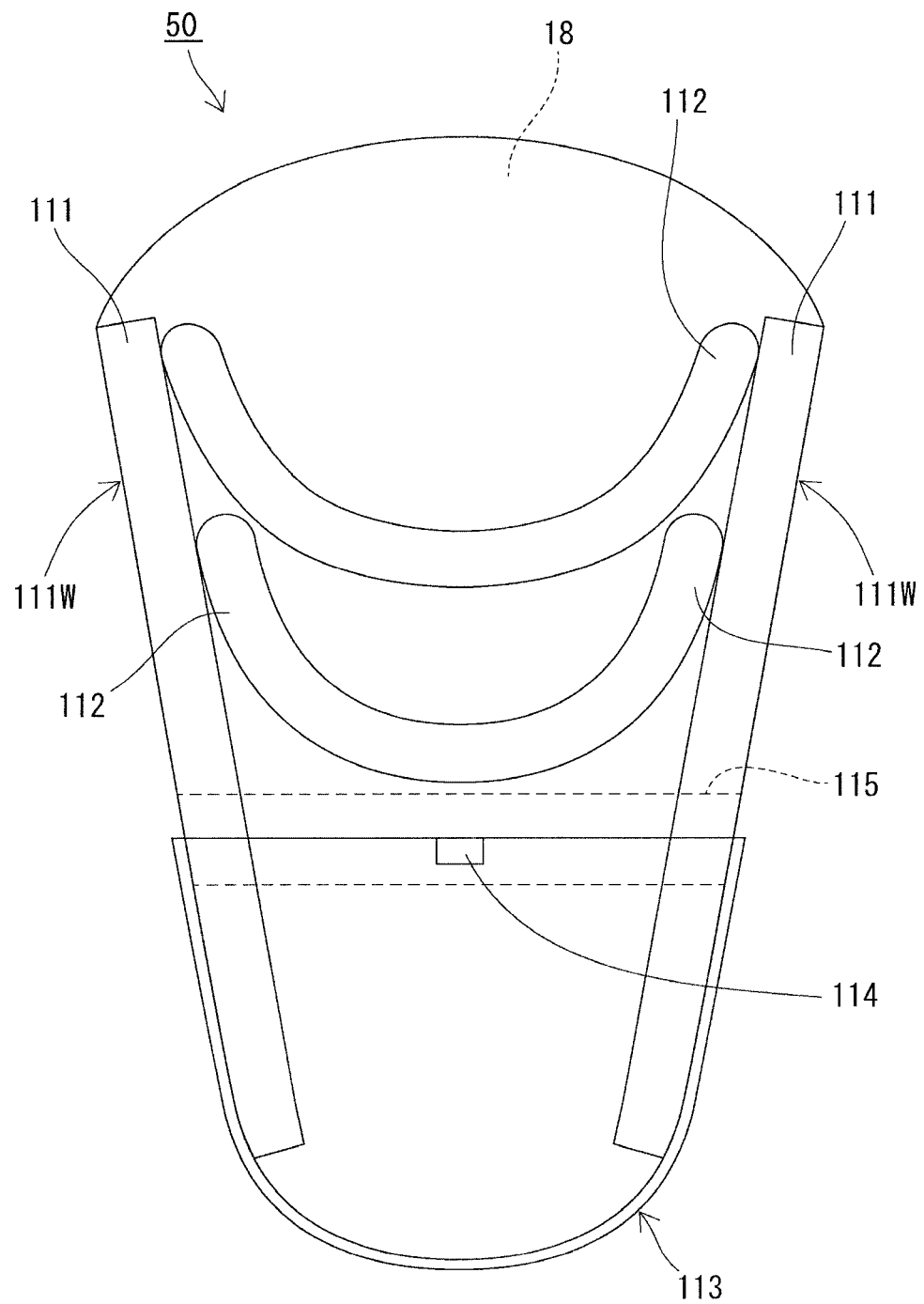
FIG. 4 is a plan view of a urine absorption pad according to a second embodiment of the present invention.
Figure 5:
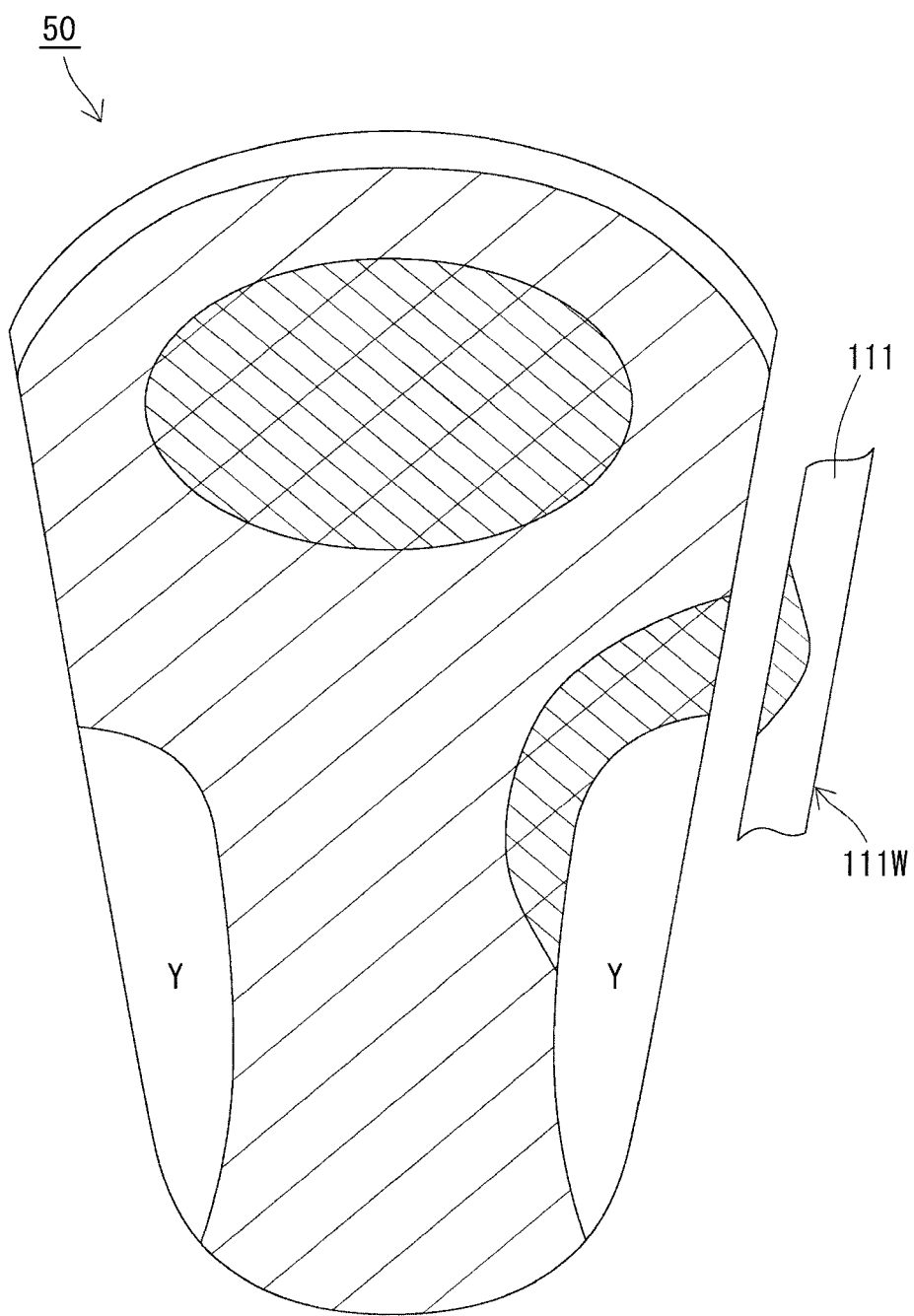
FIG. 5 is a schematic view of a urine absorption status in the second embodiment of the present invention.

FIGS. 4 and 5 show a second embodiment of a urine absorption pad according to the present invention. FIG. 4 is a plan view of the pad, and FIG. 5 is an overview of a reaction status of the absorbent 18 with the front surface sheet removed after a use experiment of the pad. A side view of the second embodiment is not shown because it is similar to FIG. 2. Reference numeral 50 in FIG. 4 denotes a urine absorption pad for men for realizing the present invention, and "Poise (registered trademark) Men's Pad" Thin and Wide 300 cc manufactured by NIPPON PAPER CRECIA Co., LTD. is used as a base material thereof.

As shown in FIG. 4, the second embodiment is the same as the first embodiment except that the arrangement of guides B 112 is different from that of the first embodiment. That is, in the second embodiment, the guide B 112 has a U shape extending in the left-right direction of the pad with the long-side direction of the guide B being the lateral direction, and two guides B 112 are arranged substantially in parallel in the longitudinal direction of the pad. The second embodiment aims to reduce cost by reducing the amount of use of the guides B as compared with the first embodiment. As the guide B 112, a cylindrical portion of "GEKIOCHI-KUN" (registered trademark) K00213 manufactured by LEC, INC.

which is the same as that of the first embodiment is appropriately divided and cut to be used.

In the use experiment, the pad according to the present invention was attached to tight-fitting pants, and after about two and a half hours, a urine discharge experiment was performed in an upright posture with both legs opened to a substantially shoulder width. In this urine discharge experiment, no leakage of urine to the outside of the system was observed. The weight of the pad of the present invention after this experiment was 245 grams. Since the initial weight after sticking all of the various guides and the like was 29 g, the difference 216 g is the weight of urine, and assuming that the urine specific gravity is 1, 216 cc could be absorbed and captured without leaking to the outside of the system.

FIG. 5 is an overview of the reaction status of the absorbent 18 with the front surface sheet 16 removed after the experiment. The single hatched portion is a yellowed portion. The double hatched portion is a portion that has been more deeply yellowed than the single hatched portion. On the other hand, a white unreacted portion slightly remains at the upper end of the pad. The regions Y in FIG. 5 are also white unreacted portions. This is the result of the absorbent 18 which did not react with urine due to the flow of urine hindered by compression of both thighs against the pad. As is clear from the comparison with FIG. 3, it is considered that this is because the guide B 112 is only arranged to be curved in a U shape and does not extend to the lower end of the pad in the second embodiment, while the guide B 12 extends to the lower end of the pad along the guide A 11 in the first embodiment.

In FIG. 5, a high reaction site of the absorbent 18 indicated by double hatching is also observed in the right-side portion of the center of the pad. In addition, urine stain is partially observed in the guide A 111 in contact with this portion of the pad. From this, the following process can be read, that is, the flow of urine struck on this portion, the guide A 111 absorbed a certain amount of urine, a water-impermeable surface 111W blocked leakage of urine to the outside of the system, the flow of urine was pushed back toward the central portion of the pad main body in the lateral direction, and urine was fixed and captured by the absorbent 18 present therein. This is the effect of the guide A 111 which is self-standing and is a porous body that is continuous voids and has water permeability and water retainability. That is, it is found that the guide A 111 prevents overflow of urine to the outside of the system.

After the experiment, the inside of a plastic bag 113 was slightly cloudy. The released urine may have flowed smoothly over the pad surface by the guides A 111 and the guides B 112, and have been mostly captured by the absorbent 18 in the process, and a part thereof may have directly reached the lower end of the pad and then have been captured by the absorbent 18. In the second embodiment, although the flow of urine is hindered by compression of both thighs against the pad, and the regions Y is formed, the flow of urine reaches the lower end of the pad, possibly due to the effect of the guides A 111, and the absorbent 18 in this portion is utilized.

The results of repeated wearing tests using the same form as that of the second embodiment are shown in Table 4.

TABLE 4

| Experiment Number | Pad Weight (g) | | Urine Absorption Capturing Amount (cc) | Presence or Absence of Leakage to Outside of System | Sense of Use |
| --- | --- | --- | --- | --- | --- |
| | Before Wearing | After Urine Discharge Test | | | |
| Example 4 | 29 | 245 | 216 | Absent | Favorable |
| Example 5 | 29 | 251 | 222 | Absent | Favorable |
| Example 6 | 29 | 228 | 199 | Absent | Favorable |

In all cases, there was no leakage of urine to the outside of the system. As for the sense of use, similarly to the first embodiment, there was a sense of wetness in the lower part of the penis and a part of the balls in contact with the penis. However, there was no particular problem in the sense of use.

Third Embodiment

Figure 6:
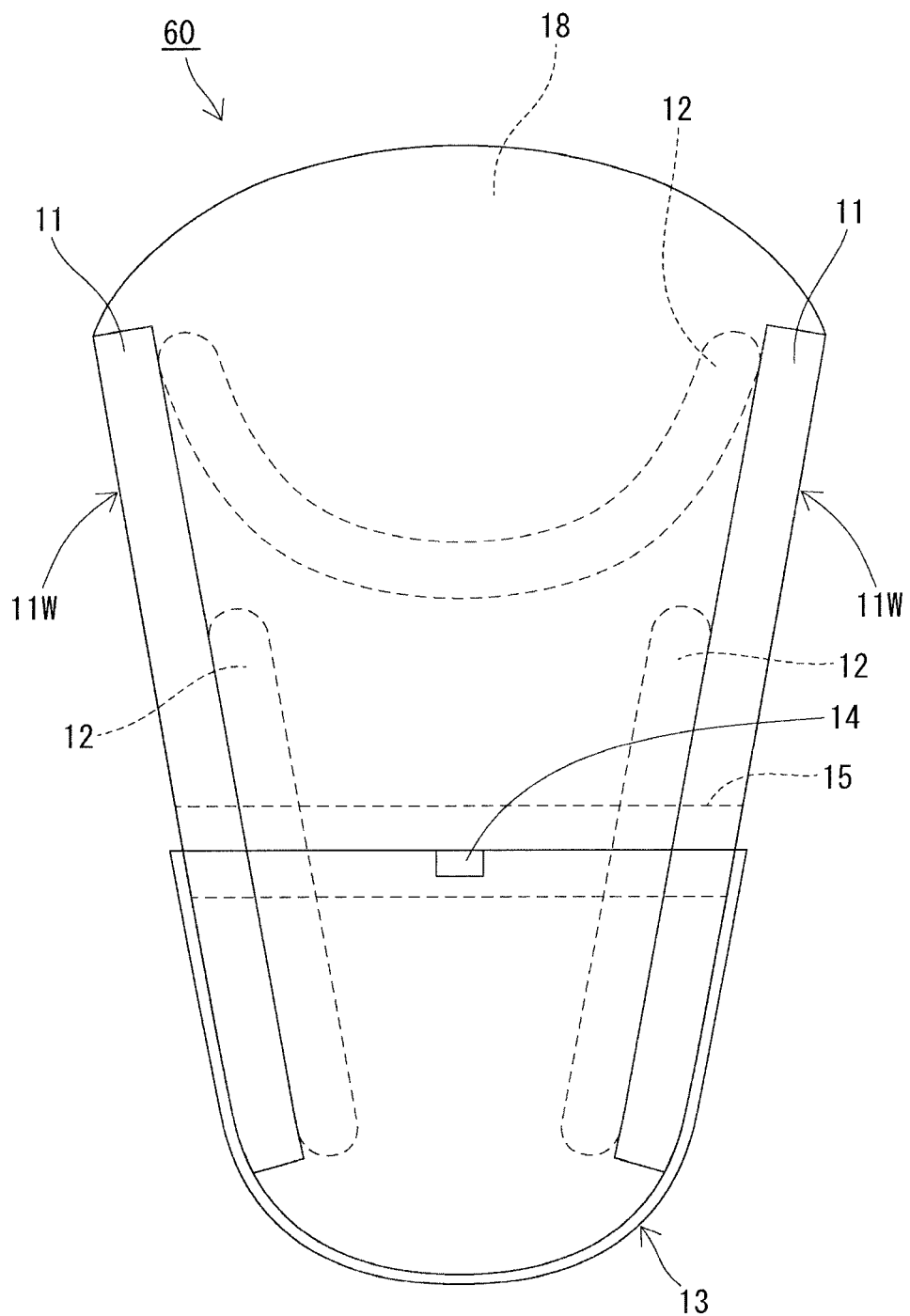
FIG. 6 is a plan view of a urine absorption pad according to a third embodiment of the present invention.
Figure 7:
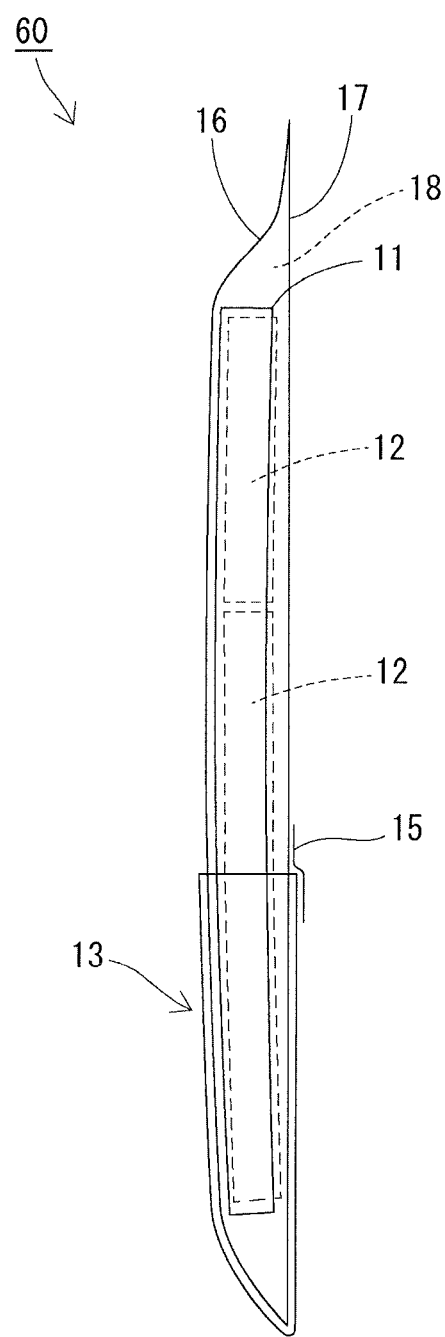
FIG. 7 is a side view of the urine absorption pad according to the third embodiment of the present invention.

FIGS. 6 and 7 show a third embodiment of a urine absorption pad according to the present invention. FIG. 6 is a plan view of the pad, and FIG. 7 is a side view of the pad. Reference numeral 60 in FIG. 6 denotes a urine absorption pad for men for realizing the present invention, and "Poise (registered trademark) Men's Pad" Thin and Wide 300 cc manufactured by NIPPON PAPER CRECIA Co., LTD. is used as a base material thereof. In the third embodiment, the guides B 12 in FIG. 1 of the first embodiment are arranged between the front surface sheet 16 which has water permeability and contacts the skin and the back surface sheet 17 which has water impermeability and contacts underwear, and the other configurations are the same as those of the first embodiment.

The constituent elements of the urine absorption pad for men for realizing the third embodiment are the same as those of the first embodiment, but are different in a preparation method. Specifically, a part of the front surface sheet 16 which has water permeability is cut open, and three guides B 12 are appropriately inserted between the front surface sheet 16 and the back surface sheet 17, and fixed to the front surface sheet 16 which has water permeability using the double-sided tape described above. The cut opening of the front surface sheet 16 which has water permeability is closed by arranging and sticking the guides A 11 thereon so as to close the opening using a double-sided tape. The preparation method of the third embodiment is the same as that of the first embodiment except for the above points. That is, the guides B 12 are self-standing so as to rise to the front surface sheet 16 side with respect to the back surface sheet 17.

In the use experiment, the pad was according to the present invention attached to tight-fitting pants, and after about two and a half hours, a urine discharge experiment was performed in an upright posture with both legs opened to a substantially shoulder width. In this urine discharge experiment, no leakage of urine to the outside of the system was observed. The weight of the pad of the present invention after this experiment was 264 grams. Since the initial weight after sticking all of the various guides and the like was 32 g, the difference 232 g is the weight of urine, and assuming that the urine specific gravity is 1, 232 cc could be absorbed and captured without leaking to the outside of the system.

The front surface sheet 16 was removed after the experiment and a reaction status of the absorbent 18 was observed. Since the yellowed region is almost the same as that in FIG. 3, it is not shown. Since the guides B 12 were arranged between the front surface sheet 16 and the back surface sheet 17 and in the absorbent 18, the particles of the reacted absorbent 18 were attached so as to cling to the entire guides B 12.

The results of repeated wearing tests using the same form as that of the third embodiment are shown in Table 5.

TABLE 5

| Experiment Number | Pad Weight (g) | | Urine Absorption Capturing Amount (cc) | Presence or Absence of Leakage to Outside of System | Sense of Use |
| --- | --- | --- | --- | --- | --- |
| | Before Wearing | After Urine Discharge Test | | | |
| Example 7 | 32 | 264 | 232 | Absent | Favorable |
| Example 8 | 32 | 248 | 216 | Absent | Favorable |
| Example 9 | 32 | 225 | 193 | Absent | Favorable |

In all cases, there was no leakage of urine to the outside of the system. As for the sense of use, similarly to the first embodiment, there was a sense of wetness in the lower part of the penis and a part of the balls in contact with the penis. However, there was no particular problem in the sense of use. In the first embodiment, the guides B 12 directly contact with the skin, whereas in the third embodiment, the front surface sheet 16 is interposed between the guides B 12 and the skin, and thus it was expected that there was a difference in wearing feeling. However, there was no significant difference.

Fourth Embodiment

Figure 8:
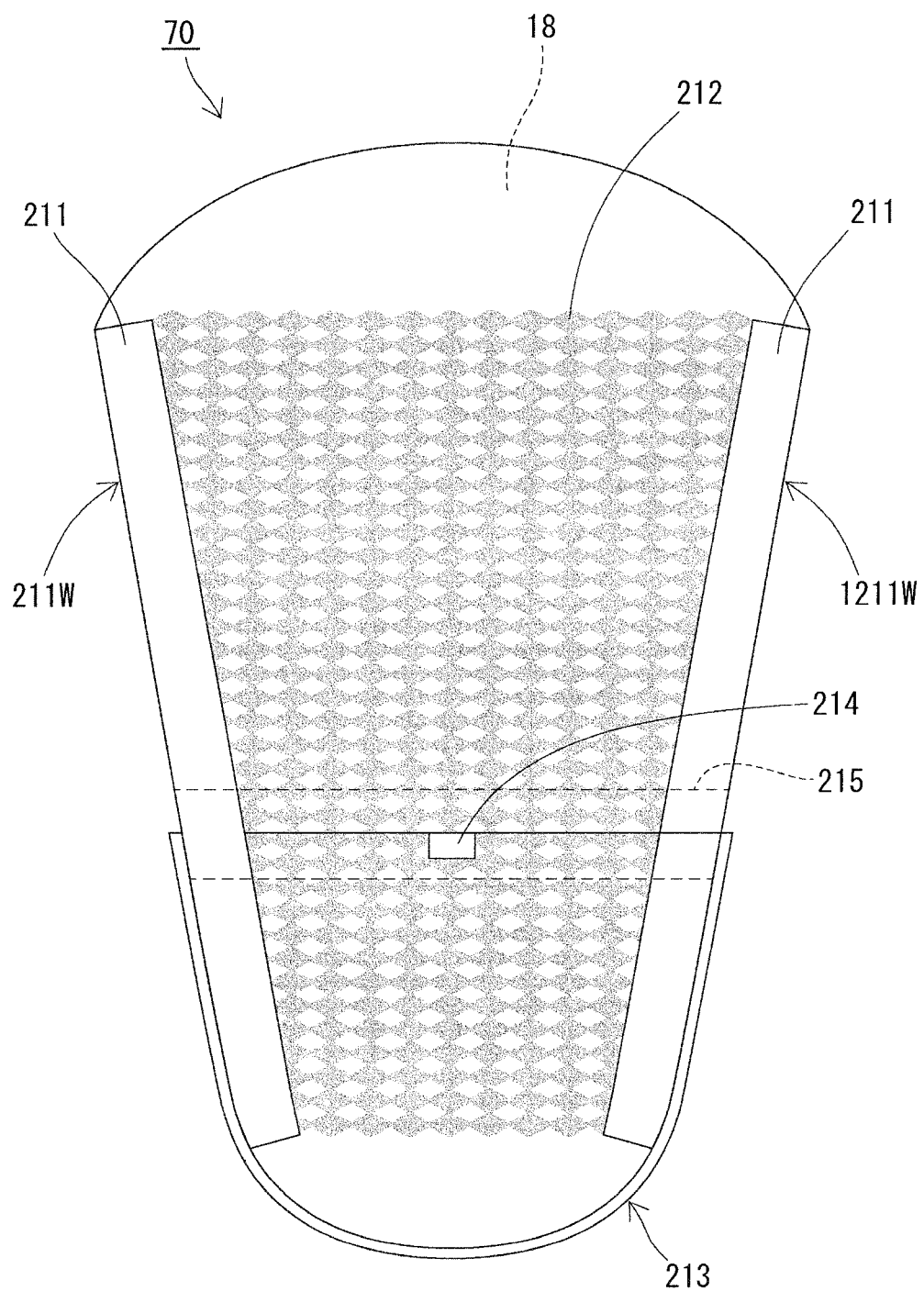
FIG. 8 is a plan view of a urine absorption pad according to a fourth embodiment of the present invention.
Figure 9:
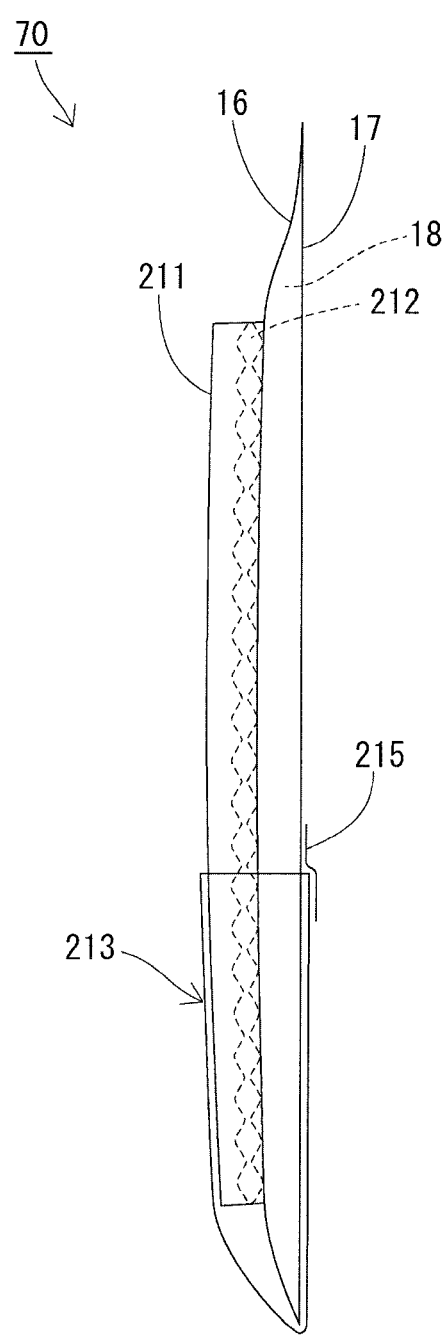
FIG. 9 is a side view of the urine absorption pad according to the fourth embodiment of the present invention.
Figure 10:
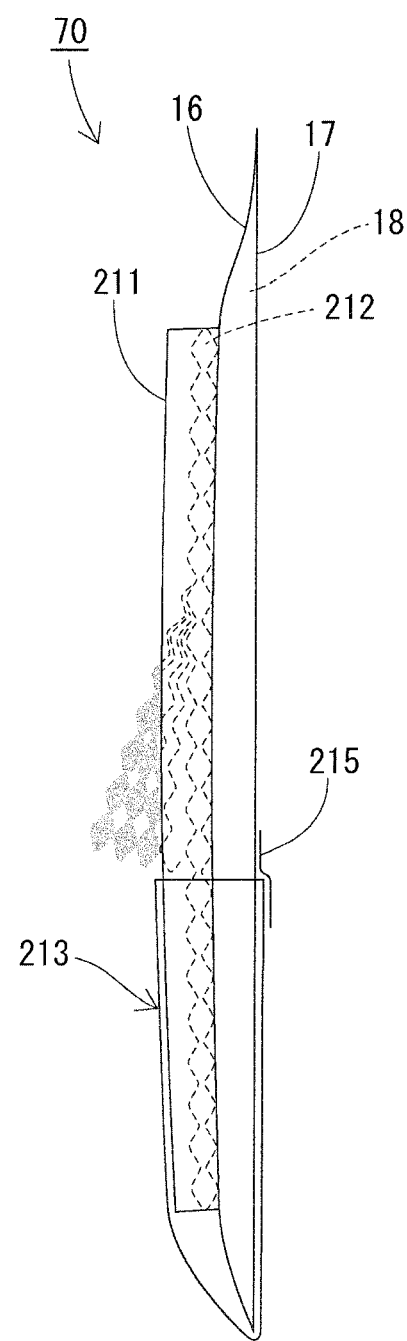
FIG. 10 is a side view of the urine absorption pad in which an arrangement of a mesh body is changed in the fourth embodiment of the present invention.
Figure 11:
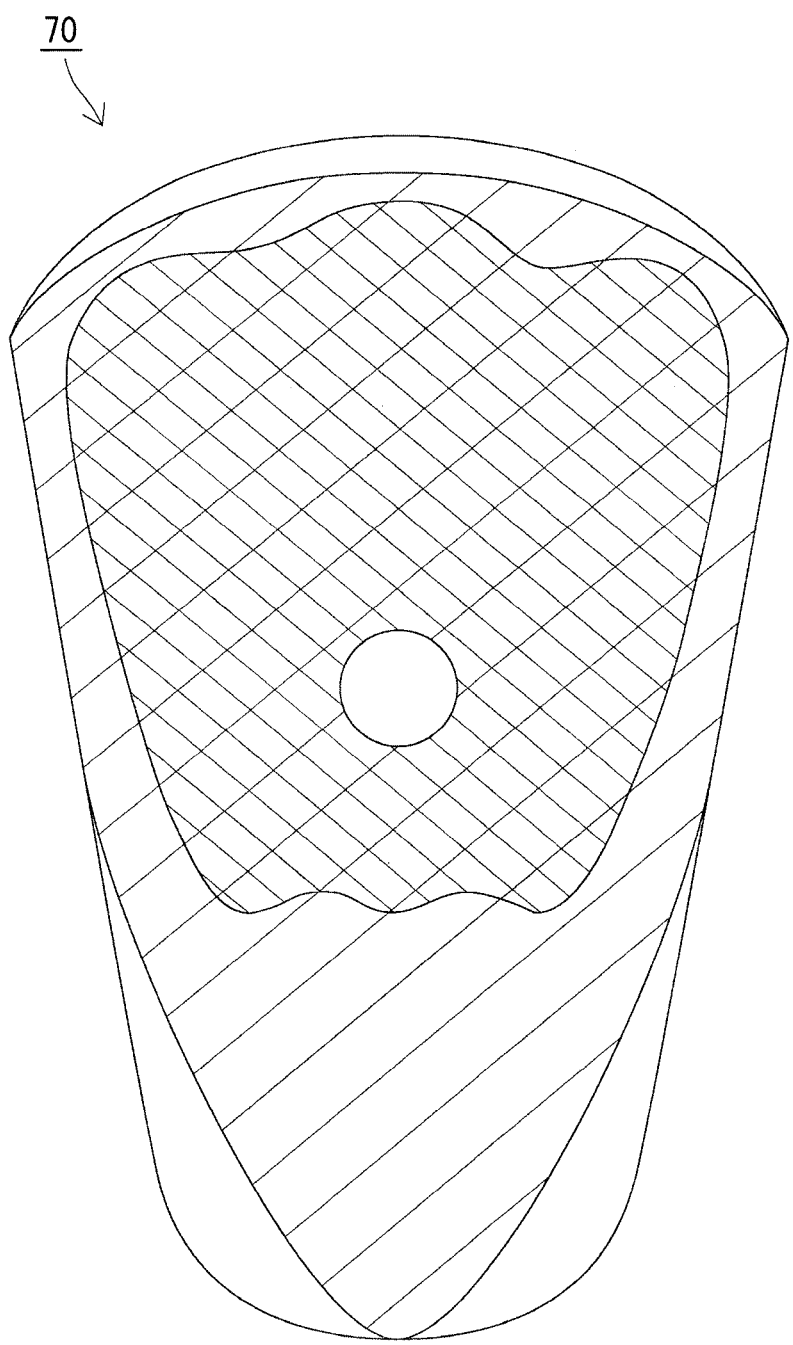
FIG. 11 is a schematic view of a urine absorption status in the fourth embodiment of the present invention.

FIGS. 8 to 11 show a fourth embodiment of a urine absorption pad according to the present invention. FIG. 8 is a plan view of the pad according to the fourth embodiment, FIG. 9 is a side view thereof, and FIG. 10 is a side view of the pad according to another example. Reference numeral 70 in FIG. 8 denotes a urine absorption pad for men for realizing the present invention, and "Poise (registered trademark) Men's Pad" Thin and Wide 300 cc manufactured by NIPPON PAPER CRECIA Co., LTD. is used as a base material thereof. In the fourth embodiment, instead of arranging the guides B 12 in FIG. 1 of the first embodiment, a mesh body 212 is arranged on the front surface sheet 16. FIG. 10 shows a state in which the width of the mesh body 212 is made larger than the width of the inside of the pad defined by the guides A 211 in the central portion and the lower side of the pad in the longitudinal direction, whereby the direction in which the mesh body 212 spreads is changed by the guides A 211, and the mesh body 212 is self-standing so as to be higher than the guides A 211 (that is, in a state of being farther away from the front surface sheet 16 than the guides A 211). As a result, even when the distance between the pad and the wearer accidentally increases for some reason after the wearer wears the pad, the gap is expected to be filled with the mesh body 212. FIG. 11 is an overview of a reaction status of the absorbent 18 with the front surface sheet 16 removed after the use experiment of the pad.

The constituent elements of the urine absorption pad for men of 70 for realizing the present embodiment are the same as those of the first embodiment except that the mesh body 212 is used as the guides B. As the mesh body 212, Non-slip Mat LFB-60 manufactured by ASAHIPEN CORPORATION was appropriately cut and used. The said product has a thickness of about 3 mm, and is formed such that a plurality of particles which are synthetic resin foam having a generally long spherical shape are arranged and connected in two directions of a long-side direction and a short-side direction. These particles are foam which is continuous voids and thus have a function of retaining water. By arranging such a mesh body 212 on the entire surface of the front surface sheet 16, it can be expected that a space is provided between the wearer and the pad, and a flow of urine is guided to the entire surface of the pad along the mesh body 212.

In the use experiment, the pad according to the present invention was attached to tight-fitting pants, and after about two and a half hours, a urine discharge experiment was performed in an upright posture with both legs opened to a substantially shoulder width. In this urine discharge experiment, no leakage of urine to the outside of the system was observed. The weight of the pad of the present invention after this experiment was 264 grams. Since the initial weight after sticking all of the various guides and the like was 35 g, the difference 229 g is the weight of urine, and assuming that the urine specific gravity is 1, 229 cc could be absorbed and captured without leaking to the outside of the system.

FIG. 11 is an overview of the reaction status of the absorbent 18 with the front surface sheet 16 removed after the experiment. The single hatched portion is a yellowed portion. The double hatched portion is a portion that has been more deeply yellowed than the single hatched portion. The single hatched portion is slightly narrow on the lower side of the pad, and it is considered that the amount of urine that has reached the lower side of the pad was smaller than that in the first embodiment. On the other hand, the double hatched portion spreads over the entire region from the upper portion to the central portion of the pad, and it is considered that absorption reaction of most of the urine occurred here. There is a white unreacted portion at substantially the central portion of the pad. This indicates that urine did not reach the portion due to pressing of the balls, so that absorption of urine did not occur.

The results of repeated wearing tests using the same form as that of the fourth embodiment are shown in Table 6.

TABLE 6

| Experiment Number | Pad Weight (g) | | Urine Absorption Capturing Amount (cc) | Presence or Absence of Leakage to Outside of System | Sense of Use |
| --- | --- | --- | --- | --- | --- |
| | Before Wearing | After Urine Discharge Test | | | |
| Example 10 | 35 | 264 | 229 | Absent | Average |
| Example 11 | 35 | 231 | 196 | Absent | Average |
| Example 12 | 35 | 247 | 212 | Absent | Average |

In Table 6, the sense of use was "Average" because the sense of wetness reached the lower part of the penis and the entire balls after the test.

Fifth Embodiment

FIGS. 12 to 15 show another fifth embodiment of the urine absorption pad according to the present invention. Unlike the first to fourth embodiments, the fifth embodiment is premised on use in a sitting posture. In the case of the sitting posture, not only the balls but also the thighs are greatly pressed against the upper surface of the pad as compared with the standing posture, and there is a high possibility that the flow of urine in the pad is hindered. For this reason, it is one idea to arrange a guide B that is resistant to pressing and has rigidity on the pad, but there is also a possibility that the sense of use may decrease. Thus, it is aimed to absorb most of the discharged urine at the front side where the pressing force is not easily applied.

Figure 12:
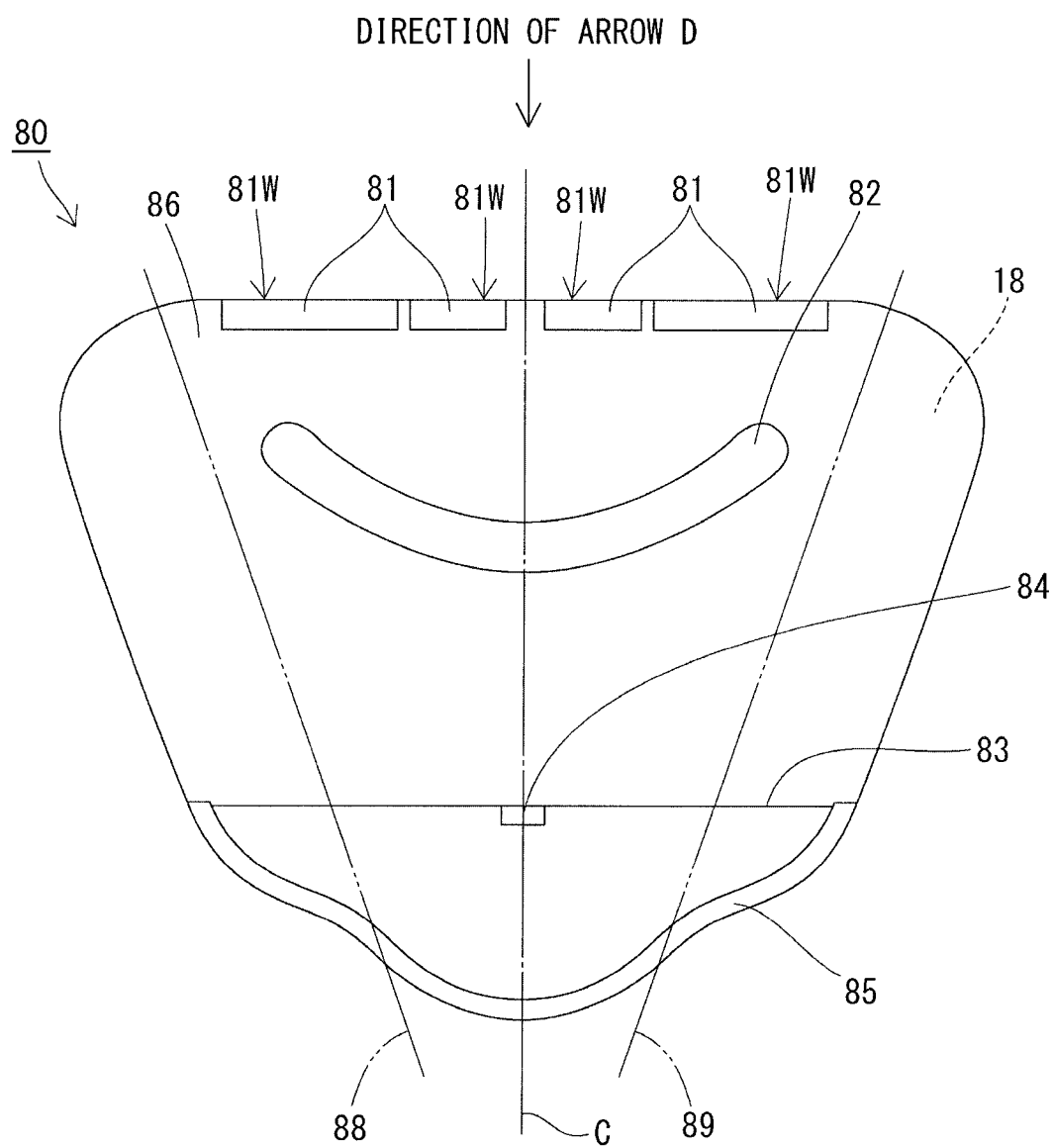
FIG. 12 is a plan view of a urine absorption pad according to a fifth embodiment of the present invention.

Therefore, as shown in FIG. 12, in the urine absorption pad according to the fifth embodiment, the width on the front side is formed to be larger than the width on the rear side. In the direction of being worn on the body of the wearer, the absorbent 18 is arranged generally throughout a urine absorption pad 80. The portion where the absorbent 18 is arranged is longer in the lateral direction than in the longitudinal direction. The amount of the absorbent 18 on the front side is greater than on the rear side. The vicinities of the intersections of the lower edge portion of the urine absorption pad 80 and two-dot chain lines 88 and 89 are formed to be recessed toward the front side.

Reference numeral 81 denotes a guide A located at the uppermost edge portion in the longitudinal direction which is a pad edge portion, and "GEKIOCHI PAPA" S-693 manufactured by LEC, INC. is appropriately cut and formed into a 15 mm square to be used. The guides A of 81 close to the center line C are fixed to the upper surface of the pad with the above-described double-sided tape (not shown) at an interval of about 10 mm. The guides A of 81 located at both ends are fixed to the upper surface of the pad with the above-described double-sided tape (not shown) similarly to the guides A close to the center line C, at an interval of several mm from the guide A close to the center line C. This is because when the pad is worn, the pad is bent into a substantially W shape when viewed from the viewpoint of the wearer, so that the guides A of 81 close to the center line C interfere with each other and become difficult to bend, and the gap between the skin surface of the wearer and the pad is increased.

A cellophane tape is stuck to the outermost surface of the guide A, which is a surface facing the outside of the system, so that the outermost surface 81W of the pad has water impermeability. This is to prevent urine from permeating or passing over 81 and leaking.

Reference numeral 82 denotes a guide B, a cylindrical portion having a diameter of about 18 mm of "GEKIOCHI-KUN" (registered trademark) K00213 manufactured by LEC, INC. is appropriately divided and cut to be used, and the guide B 82 is fixed to the upper surface of the pad using the above-described double-sided tape (not shown). This is for making the flow of urine in front of the pad 80 spread laterally.

Reference numeral 83 denotes a food wrap film. This is for guiding urine to prevent leakage of urine from the lower end of the pad of the present invention when urine reaches the lower end in a liquid state before being absorbed by the adsorbent. The food wrap film 83 is fixed to a front surface sheet 86 having water permeability with a double-sided tape of 85 (using the above-mentioned material). If the opening portion of the food wrap film 83 is in a free state, urine may leak from the opening portion. Therefore, the central portion of the opening portion of the food wrap film 83 is stuck to the front surface sheet 86 using the double-sided tape 84 described above.

Figure 13:
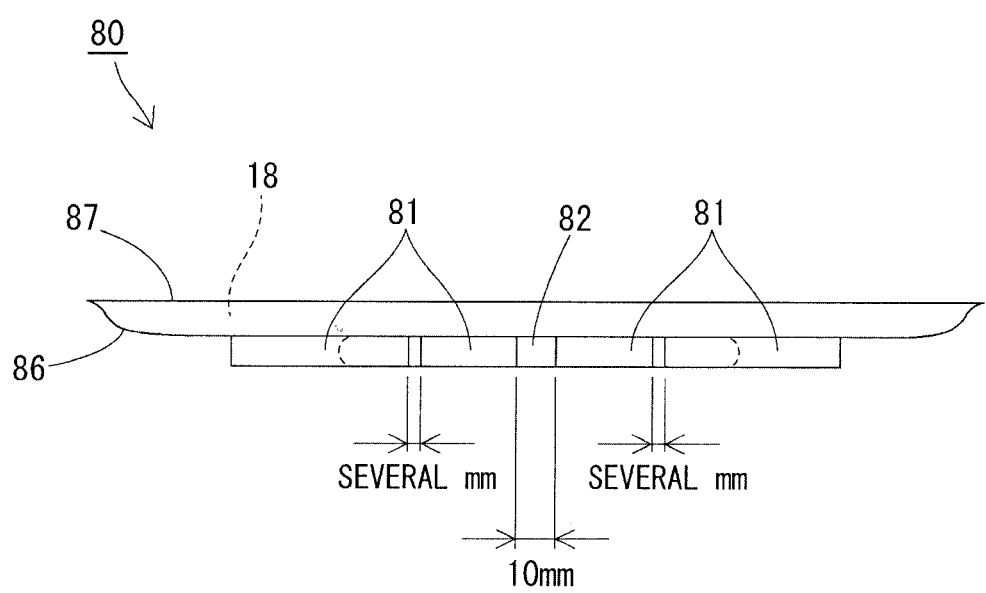
FIG. 13 is a side view of the urine absorption pad according to the fifth embodiment of the present invention.

FIG. 13 is a side view of the pad of the present invention as viewed in a direction of arrow D. Reference numeral 86 denotes the front surface sheet of the pad of the present invention, which is mainly a sheet having water permeability. Reference numeral 87 is a back surface sheet of the pad of the present invention, which has water impermeability. Between the sheets 86 and 87, the absorbent 18 for absorbing urine is contained. It can be seen that the guide A 81 has a constant height on the upper surface of the pad. In FIG. 13, the visible surface of the guide A 81 is a water-impermeable surface. The two-dot chain lines 88 and 89 in FIG. 12 are bent lines that are bent by being sandwiched between the crotches when the pad is worn.

Figure 14:
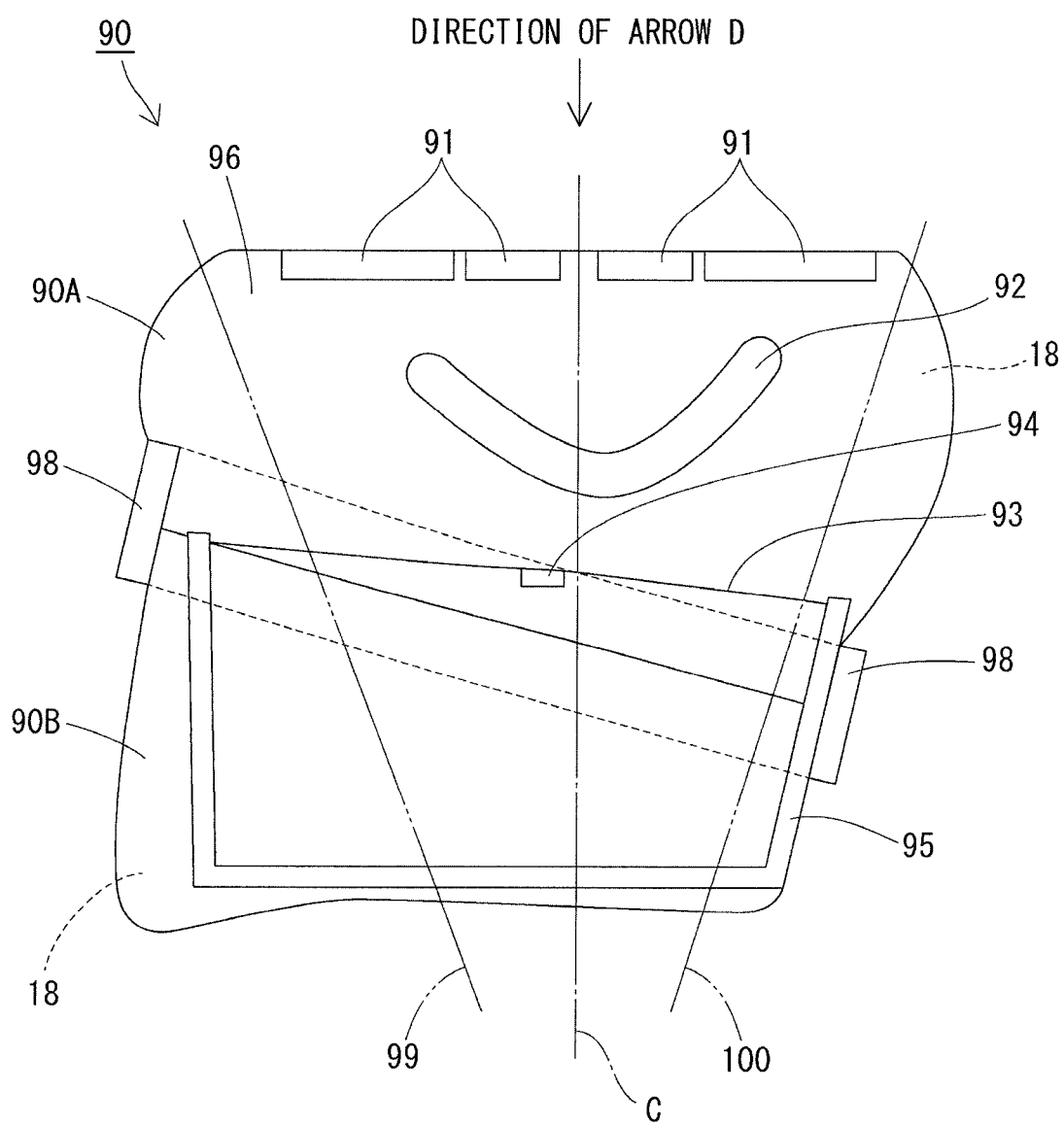
FIG. 14 is a plan view of a urine absorption pad prepared for carrying out a urine discharge experiment in the fifth embodiment of the present invention.
Figure 15:
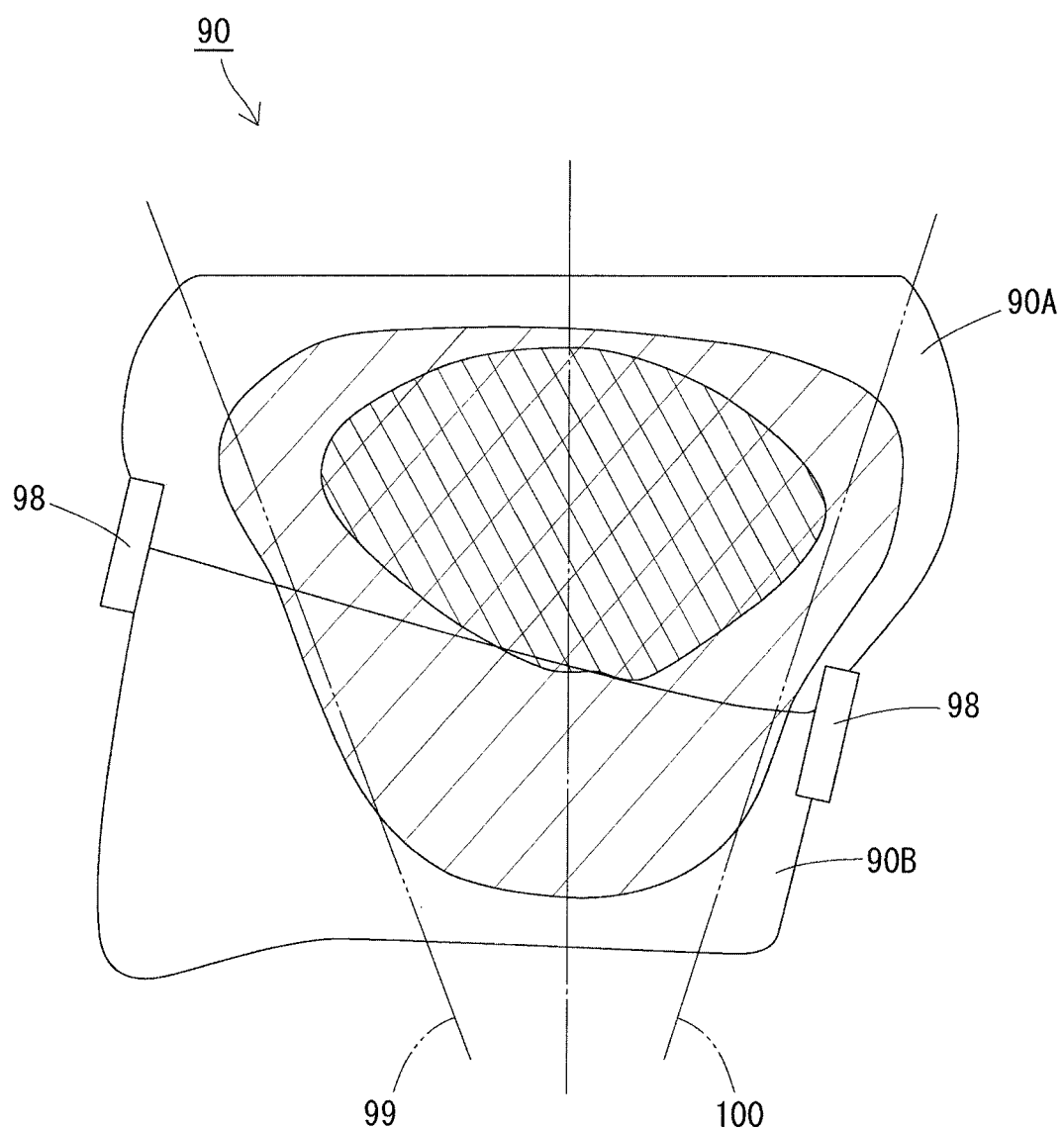
FIG. 15 is a schematic view of a urine absorption status in the fifth embodiment of the present invention.

Reference numeral 90 in FIG. 14 schematically indicates the pad according to the fifth embodiment in FIGS. 12 and 13 using a commercially available urine absorption pad, and FIG. 15 is an overview of a reaction status of the absorbent 18 with a front surface sheet 96 removed after the use experiment of the pad. In the urine absorption pad 90, as a base material of the pad, a first pad 90A ("Poise (registered trademark) Men's Pad" Thin and Wide 300 cc manufactured by NIPPON PAPER CRECIA Co., LTD.) and a second pad 90B (Lifree (registered trademark) Men's Refreshing Thin Pad 120 cc manufactured by Unicharm Corporation) are connected to be adjacent to each other using a packing tape. It is assumed that the first pad 90A contains the absorbent 18 in an amount capable of absorbing at least 300 cc of urine. It is assumed that the second pad 90B contains the absorbent 18 in an amount capable of absorbing at least 120 cc of urine. In the urine absorption pad 90, the portion where the absorbent 18 is arranged is longer in the lateral direction than in the longitudinal direction in the direction of being worn on the body of the wearer. The urine absorption pad 90 is intended to absorb most of urine discharged at the front side (that is, the upper part 90A side of the urine absorption pad 90) where is free from the pressure of the balls and the thighs.

Therefore, the first pad 90A capable of absorbing about 300 cc of urine is used in the upper part of the pad, and the second pad 90B capable of absorbing about 120 cc of urine is complementarily used in the lower part of the pad. The respective absorption surfaces are brought into close contact with each other, and fixed using a packing tape from the back surface side. The broken line in FIG. 14 represents the packing tape on the back surface. Reference numeral 98 denotes both end portions of the packing tape, which are folded back to partially cover the upper surface (front surface sheet 96 side) of the pad in order to prevent leakage from the joint.

Reference numeral 91 denotes a guide A, and "GEKI-OCHI PAPA" S-693 manufactured by LEC, INC. is appropriately cut and formed into a 15 mm square to be used. The guides A 91 close to the center line C are fixed to the upper surface of the pad with the above-described double-sided tape (not shown) at an interval of about 10 mm. The guides A 91 located at both ends are fixed to the upper surface of the pad with the above-described double-sided tape (not shown) similarly to the guides A close to the center line C, at an interval of several mm from the guide A close to the center line C. This is because when the pad is worn, the pad is bent into a substantially W shape when viewed from the viewpoint of the wearer, so that the guides A 91 close to the center line C interfere with each other and become difficult to bend, and the gap between the skin surface of the wearer and the pad is increased.

Reference numeral 92 denotes a guide B, a cylindrical portion having a diameter of about 18 mm of "GEKIOCHI-KUN" (registered trademark) K00213 manufactured by LEC, INC. is appropriately divided and cut to be used, and the guide B 92 is arranged on the upper surface of the pad in a U shape extending in the left-right direction of the pad with the long-side direction of the guide B being the lateral direction using the above-described double-sided tape (not shown). This is for making the flow of urine on the upper surface of the first pad 90A spread laterally.

Reference numeral 93 denotes a food wrap film. This is to guide urine to prevent leakage of urine from the lower end of the pad when urine reaches the lower end in a liquid state before being absorbed by the adsorbent. The food wrap film 93 is fixed to the upper surface of the second pad 90B with a double-sided tape 95 (using the above-mentioned material). If the opening portion of the food wrap film 93 is in a free state, urine may leak from the opening portion. Therefore, the central portion of the opening portion of the food wrap film 93 is stuck to the upper surface of the first pad 90A using the double-sided tape 94 described above. The two-dot chain lines 99 and 100 are bent lines that are bent by being sandwiched between the crotches when the pad is worn. The total weight of the urine absorption pad 90 of the fifth embodiment complete with these pieces of equipment is 48 grams.

In the use experiment, the urine absorption pad 90 was attached to tight-fitting pants, and after about two hours, the wearer sat on the lid of the Western style toilet bowl, opened his/her both legs to a substantially shoulder width, and a urine discharge experiment was performed in a sitting posture. The pad according to the fifth embodiment is attached such that the guides A 91 are arranged in the lateral direction with respect to the wearer and located at the upper end. That is, the urine absorption pad 90 is worn by wearer such that the orientation of the first pad 90A and the second pad 90B intersects the orientation of the state in which the first pad 90A and the second pad 90B are used alone.

In this urine discharge experiment, no leakage of urine to the outside of the system was observed. The weight of the fifth embodiment after this experiment was 255 grams. Since the initial total weight was 48 g, the difference 207 g is the weight of urine, and assuming that the urine specific gravity is 1, 207 cc of the difference 207 g could be absorbed and captured without leaking to the outside of the system.

FIG. 15 is an overview of the reaction status of the absorbent 18 with the front surface sheet 96 removed after the experiment. The single hatched portion is a yellowed portion. The yellowed portion continues from the first pad 90A to the second pad 90B. The double hatched portion is a portion that has been more deeply yellowed than the single hatched portion. A white unreacted portion remains on the upper side of the first pad 90A, and thus there is a capability of further absorption of urine.

No water droplets were found in the food wrap film 93 after the use experiment. However, when the amount of released urine increases, it is considered that there is a possibility that a part of urine directly reaches the lower end of the second pad 90B similarly to the first embodiment. Therefore, the entire front surface sheet 96 in the second pad 90B may be covered by a water-impermeable guide film.

The results of repeated wearing tests using the same form as that of the fifth embodiment are shown in Table 7.

TABLE 7

| Experiment Number | Pad Weight (g) | | Urine Absorption Capturing Amount (cc) | Presence or Absence of Leakage to Outside of System | Sense of Use |
| --- | --- | --- | --- | --- | --- |
| | Before Wearing | After Urine Discharge Test | | | |
| Example 13 | 48 | 255 | 207 | Absent | Average |
| Example 14 | 48 | 234 | 186 | Absent | Average |
| Example 15 | 48 | 266 | 218 | Absent | Average |

In Table 7, the sense of use was "Average" because the sense of wetness reached the lower part of the penis and the entire balls after the test.

In the urine absorption pad 90, the portion where the absorbent 18 gathers is longer in the lateral direction than in the longitudinal direction in the direction of being worn on the body of the wearer. With this configuration, even when the wearer is in a seated posture and the flow of urine to the back of the balls is hindered by pressing of the balls or the like, the entire amount of urine can be absorbed without leakage of urine to the outside of the system since most of the part for absorbing urine exists in front of the balls.

<Form of Existing Commercially Available Pad>

Figure 16:
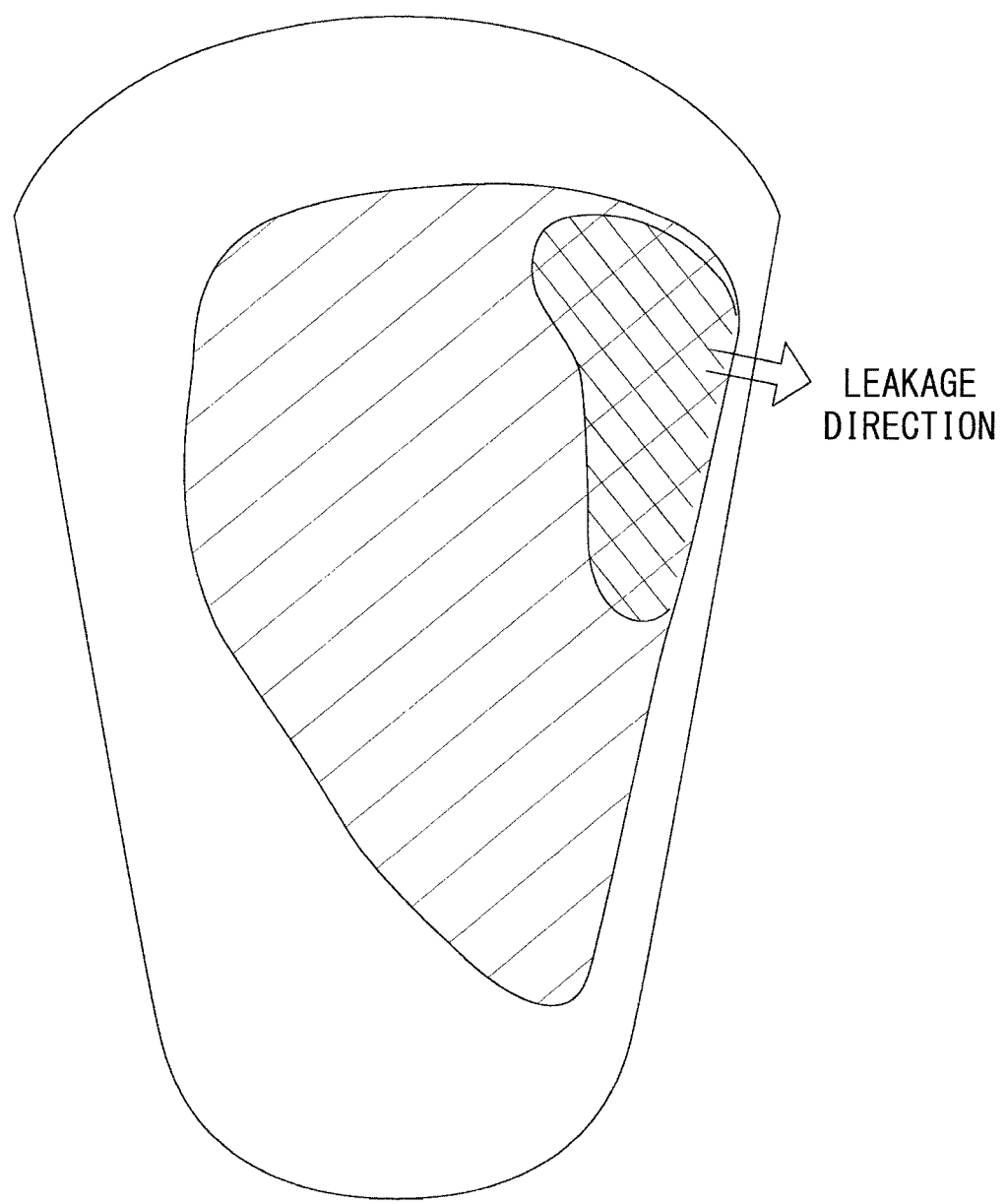
FIG. 16 is a schematic view of a urine absorption status in an existing commercially available urine absorption pad for men.

FIG. 16 is a schematic view of a urine absorption status in an existing commercially available urine absorption pad for men from which a front surface sheet is removed. This corresponds to Comparative Example. In a use experiment of the existing commercially available pad, "Poise (registered trademark) Men's Pad" Thin and Wide 300 cc manufactured by NIPPON PAPER CRECIA Co., LTD. was attached to tight-fitting pants, and after about two and a half hours, a urine discharge experiment was performed in an upright posture with both legs opened to a substantially shoulder width.

Leakage of urine to the outside of the system started in the middle of the urine discharge test. Since urination cannot be interrupted as described above, the pad was taken out after all urine was discharged, and the weight thereof was measured and found to be 122 g. The weight of the pad before use was 25 grams, so the difference was 97 grams, and assuming that the urine specific gravity is 1, 97 cc of urine was captured. As shown in FIG. 16, when the status of urine absorption is observed, the single hatched portion is a yellowed portion, and a portion that has been more deeply yellowed than the single hatched portion is indicated by the double hatched portion. The double hatched portion had a thickness increased by about 3 to 4 times the thickness of the periphery. It can be seen that when urine flows in nearby this portion, the absorbent of this portion chemically changes quickly and fixes the urine, and at the same time, the volume of the portion was remarkably increased, which prevented the subsequent urine flow from moving downward from this portion, and in addition, the urine flow continued beyond the fixable urine amount by the chemical change in the vicinity of this portion, resulting in occurrence of urine leakage. The path through which urine may have overflowed from the pad is indicated by an arrow.

In addition, an existing overflow prevention measure is a sheet, which is suspended by an elastic body such as rubber, to which a pad is attached, and which is bent and made to be in a rising state from a flat state to prevent overflow of urine, and after it is worn, a certain height is maintained regardless of release of urine. As described above, since the thickness of the vicinity of the location where urine has flowed in is increased by about 3 to 4 times the thickness of the periphery, the existing overflow preventing sheet loses a relative height difference and does not serve to prevent overflow. This is also considered to be a cause of occurrence of urine leakage.

The existing commercially available pad has poor flow of urine in the pad. In addition, the existing commercially available pad does not have a function of correcting a urine release direction when the urine release direction is biased, so that urine is biasedly absorbed, and also an absorbent chemically changes and greatly expands the volume, which becomes an obstacle that hinders the urine flow in the pad. Due to this, urine does not spread to other portions where the urine absorption capacity remains, and urine overflows when the absorption capacity of the portion where urine is biasedly absorbed reaches the limit, which leads to leakage of urine.

The present invention is not limited to the embodiments described with reference to the above description and drawings. For example, the following embodiments are also included in the technical scope.

(1) In the fourth embodiment, the material of the guide B is different from that of the guide B in the first to third embodiments and the fifth embodiment. However, the present invention is not limited thereto, but the material of the guide B in the fourth embodiment and the material of the guide B in the first to third embodiments and the fifth embodiment may be used in combination. The material of the guide B is not limited to the material used in the present embodiments, but another material not containing the superabsorbent polymer may be used as the guide B. Furthermore, the material of the guide A is not limited to the material used in the present embodiments, but another material not containing the superabsorbent polymer may be used as the guide A.

(2) The guide A and the guide B each having the double-sided tape attached thereto may be attached later to a commercially available urine absorption pad. That is, these guide A and guide B can be freely attached to the wearer's skin side surface of the front surface sheet that contacts the skin of the wearer of the urine absorption pad which absorbs urine of the wearer. The guide A and the guide B allow urine to permeate and are self-standing so as to rise to the skin side of the wearer from the front surface sheet to control the flow of urine. With this configuration, since the positions where the guide A and the guide B are attached can be adjusted according to the state of the body of the wearer, not only urine can be more favorably absorbed with a commercially available urine absorption pad, but also the feel of wearing can be adjusted according to the preference of each wearer.

(3) The mesh body in the fourth embodiment is formed such that a plurality of particles, which are synthetic resin foam having a generally long spherical shape, are arranged and connected in two directions of the long-side direction and the short-side direction. However, the configuration of the mesh body is not limited thereto.

REFERENCE SIGNS LIST 10 first embodiment
11, 81, 91, 111, 211 guide A (guide)
12, 42, 82, 92, 112, 212 guide B (guide)
13, 43, 113, 213 kitchen plastic bag
14, 44, 84, 94, 114, 214 double-sided tape.
15, 45, 85, 95, 115, 215 cellophane tape
16, 46, 86, 96 front surface sheet
17, 47, 87 back surface sheet
18 absorbent
50 second embodiment
60 third embodiment
70 fourth embodiment
80, 90 fifth embodiment
90A first pad
90B second pad
83, 93 food wrap film
88, 98 folded part of packing tape
212 mesh body (guide B)

The invention claimed is:

1. A urine absorption pad system comprising:
a front surface sheet that has water permeability and contacts a skin;
a back surface sheet that has water impermeability and contacts underwear;
an absorbent that is sandwiched between the front surface sheet and the back surface sheet and absorbs urine having passed through the front surface sheet; and
a guide A and a guide B that are self-standing so as to rise to the front surface sheet side with respect to the absorbent and that allow urine to permeate to control flow of urine,
wherein the guide A and the guide B are separate bodies, are porous bodies that have continuous voids and water permeability, and which do not contain a superabsorbent polymer,
wherein the guide A has higher water retainability than the guide B, has water impermeability provided at an outermost surface facing an outside of the system, and prevents overflow of urine outside of the system,
wherein the guide B has a U shape and is arranged so as to extend in a left-right direction of the urine absorption pad system, and
wherein the guide A is arranged along an edge portion of the absorbent in a longitudinal direction, perpendicular to the left-right direction of the urine absorption pad system, and extends below the guide B in the longitudinal direction.

2. The urine absorption pad system according to claim 1, wherein the guide B allows urine to flow inside, and disperses urine in a lateral direction.

* * * * *